(12) United States Patent
Franklin

(10) Patent No.: US 8,557,958 B1
(45) Date of Patent: Oct. 15, 2013

(54) COMPOSITIONS AND METHODS FOR TREATMENT OF DIABETES

(71) Applicant: Tarix Pharmaceuticals Ltd., Cambridge, MA (US)

(72) Inventor: Richard Franklin, Cambridge, MA (US)

(73) Assignee: Tarix Pharmaceuticals Ltd., Cambridge, MA (US)

( * ) Notice: Subject to any disclaimer, the term of this patent is extended or adjusted under 35 U.S.C. 154(b) by 0 days.

(21) Appl. No.: 13/757,475

(22) Filed: Feb. 1, 2013

Related U.S. Application Data

(60) Provisional application No. 61/660,888, filed on Jun. 18, 2012, provisional application No. 61/720,296, filed on Oct. 30, 2012.

(51) Int. Cl.
- *C07K 7/14* (2006.01)
- *C07K 7/64* (2006.01)
- *A61K 38/08* (2006.01)
- *A61K 38/12* (2006.01)

(52) U.S. Cl.
USPC ............ 530/316; 514/6.8; 514/6.9; 514/16.3; 514/21.7; 514/21.9; 530/317; 530/329

(58) Field of Classification Search
None
See application file for complete search history.

(56) References Cited

U.S. PATENT DOCUMENTS

| | | | |
|---|---|---|---|
| 5,629,292 A | 5/1997 | Rodgers et al. | |
| 5,716,935 A | 2/1998 | Rodgers et al. | |
| 5,834,432 A | 11/1998 | Rodgers et al. | |
| 5,955,430 A | 9/1999 | Rodgers et al. | |
| 6,096,709 A | 8/2000 | Rodgers et al. | |
| 6,110,895 A | 8/2000 | Rodgers et al. | |
| 6,177,407 B1 | 1/2001 | Rodgers et al. | |
| 6,239,109 B1 | 5/2001 | Rodgers et al. | |
| 6,248,587 B1 | 6/2001 | Rodgers et al. | |
| 6,258,778 B1 | 7/2001 | Rodgers et al. | |
| 6,335,195 B1 | 1/2002 | Rodgers et al. | |
| 6,444,646 B1 | 9/2002 | Rodgers et al. | |
| 6,455,500 B1 | 9/2002 | Rodgers et al. | |
| 6,475,988 B1 | 11/2002 | Rodgers et al. | |
| 6,482,800 B1 | 11/2002 | Rodgers et al. | |
| 6,498,138 B1 | 12/2002 | Rodgers et al. | |
| 6,566,335 B1 | 5/2003 | Rodgers et al. | |
| 6,730,775 B1 | 5/2004 | Rodgers et al. | |
| 6,747,008 B1 | 6/2004 | Rodgers et al. | |
| 6,762,167 B1 | 7/2004 | Rodgers et al. | |
| 6,821,953 B1 | 11/2004 | Rodgers et al. | |
| 6,916,783 B2 | 7/2005 | Rodgers et al. | |
| 7,118,748 B1 | 10/2006 | Rodgers et al. | |
| 7,122,523 B2 | 10/2006 | Rodgers et al. | |
| 7,173,011 B2 | 2/2007 | Rodgers et al. | |
| 7,176,183 B2 | 2/2007 | Rodgers et al. | |
| 7,288,522 B1 | 10/2007 | Rodgers et al. | |
| 7,338,938 B2 | 3/2008 | Rodgers et al. | |
| 7,744,927 B2 | 6/2010 | Rodgers et al. | |
| 7,745,411 B2 | 6/2010 | Rodgers et al. | |
| 7,776,828 B2 | 8/2010 | Rodgers et al. | |
| 7,786,085 B2 | 8/2010 | Rodgers et al. | |
| 2008/0312129 A1 | 12/2008 | Souza Dos Santos et al. | |
| 2009/0221498 A1* | 9/2009 | Souza Dos Santos et al. | 514/12 |
| 2009/0227507 A1 | 9/2009 | Rodgers et al. | |
| 2010/0316624 A1 | 12/2010 | Loibner et al. | |
| 2011/0020315 A1 | 1/2011 | Loibner et al. | |
| 2011/0033524 A1 | 2/2011 | Janzek-hawlat et al. | |

FOREIGN PATENT DOCUMENTS

| | | |
|---|---|---|
| AU | 723373 B2 | 8/2000 |
| CA | 2205092 A1 | 5/1996 |
| CA | 2221730 A1 | 12/1996 |
| EP | 2163259 A1 | 3/2010 |
| WO | WO-95/08565 A1 | 3/1995 |
| WO | WO-96/14858 A1 | 5/1996 |
| WO | WO-96/39164 A1 | 12/1996 |
| WO | WO-98/26795 A1 | 6/1998 |
| WO | WO-98/32457 A2 | 7/1998 |
| WO | WO-99/10205 A1 | 3/1999 |
| WO | WO-99/26644 A1 | 6/1999 |
| WO | WO-99/40106 A2 | 8/1999 |
| WO | WO-99/45945 A1 | 9/1999 |
| WO | WO-99/46285 A2 | 9/1999 |
| WO | WO-99/52540 A1 | 10/1999 |
| WO | WO-00/02905 A2 | 1/2000 |
| WO | WO-00/09144 A1 | 2/2000 |
| WO | WO-00/56345 A2 | 9/2000 |
| WO | WO-01/43761 A2 | 6/2001 |
| WO | WO 01/44270 A2 * | 6/2001 |
| WO | WO-01/98325 A1 | 12/2001 |
| WO | WO-02/087504 A2 | 11/2002 |

(Continued)

OTHER PUBLICATIONS

Giani et al. ("Chronic infusion of angiotensin-(1-7) improves insulin resistance and hypertension induced by a high-fructose diet in rats," AJP—Endo Feb. 2009 vol. 296 No. 2 E262-E27).*

Rodgers et al. ("Accelerated healing of diabetic wounds by NorLeu3-angiotensin (1-7)," Expert Opin. Investig. Drugs (2011) 20(11)).*

Kluskens et al. ("Angiotensin-(1-7) with Thioether Bridge: An Angiotensin-Converting Enzyme-Resistant, Potent Angiotensin-(1-7) Analog," JPET Mar. 2009 vol. 328 No. 3 849-854).*

(Continued)

*Primary Examiner* — Christina Bradley

(74) *Attorney, Agent, or Firm* — Choate, Hall & Stewart LLP; Fangli Chen; Brian E. Reese

(57) ABSTRACT

The present invention relates to compositions and methods for treatment and/or prevention of diabetes or pre-diabetes. In particular, the invention provides compositions and methods for the treatment and/or prevention of diabetes or pre-diabetes, based on the use of angiotensin-(1-7) peptides, functional equivalents thereof, and/or angiotensin (1-7) agonists.

17 Claims, 5 Drawing Sheets

(56) References Cited

FOREIGN PATENT DOCUMENTS

| WO | WO-2008/018792 A2 | | 2/2008 |
|----|-------------------|---|--------|
| WO | WO-2009/114461 A2 | | 9/2009 |
| WO | WO 2010/028845 | * | 3/2010 |
| WO | WO-2010/028845 A2 | | 3/2010 |

OTHER PUBLICATIONS

Ebermann L. et al., The angiotensin-(1-7) receptor agonist AVE0991 is cardioprotective in diabetic rats, European Journal of Pharmacology, 590:276-280 (2008).

Fang H.J. et al., Tissue-specific Pattern of Angiotensin-converting Enzyme 2 Expression in Rat Pancreas, The Journal of International Medical Research, 38:558-569 (2010).

Jiang, T. et al., Suppressing inflammation by inhibiting the NF-kB pathway contributes to the neuroprotective effect of angiotensin-(1-7) in rats with permanent cerebral ischaemia, British Journal of Pharmacology, 167(7):1520-1532 (2012).

Mecca, A.P. et al., Cerebroprotection by angiotensin-(1-7) in endothelin-1-induced ischaemic stroke, Experimental Physiology, 96(10):1084-1096 (2011).

Mocco, J. et al., Overexpression of Angiotensin (1-7) in Hematopoietic Stem Cells: A Novel Route of Delivery in Stroke, Presentation Number: LB P21, Feb. 1, 2012.

Regenhardt, R.W. et al., Angiotensin (1-7) has therapeutic potential in hemorrhagic stroke, Physiology, University of Florida, Gainesville, FL, USA, Presentation Abstract Number: 1049, May 25-28, 2011.

Regenhardt, R.W. et al., Angiotensin (1-7) reduces cerebral cortical iNOS expression in ischemic stroke: Possible mechanism for cerebroprotection?, Presentation Abstract, Program#/Poster#: 658.7/Q9, 40th Annual Meeting Neuroscience 2010, Nov. 16, 2010.

Soto-Pantoja, D.R. et al., Angiotensin-(1-7) inhibits tumor angiogenesis in human lung cancer xenografts with a reduction in vascular endothelial growth factor, Molecular Cancer Therapeutics, 8(6):1676-1683 (2009).

Ciobica et al., Acta Neurol. Belg., 109:171-180 (2009).

Pasut et al., Exp. Opin. Ther. Pat, 14:859-894 (2004).

Santos, Robson, A.S., Pharmacological Effects of AVE 0991, a Nonpeptide Angiotensin-(1-7) Receptor Agonist, Cardiovascular Drug Reviews, 24(3-4):239-246 (2006).

Yang, L., Effects of ACE2-Ang(1-7)-Mas Mediated Pancreatic Endothelial Function on Beta Cell Function in Rats, PhD thesis, Huazhong University of Science and Technology (2011).

* cited by examiner

```
SEQUENCE LISTING

<160> NUMBER OF SEQ ID NOS: 22

<210> SEQ ID NO 1
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 1

Asp Arg Val Tyr Ile His Pro
1               5

<210> SEQ ID NO 2
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle

<400> SEQUENCE: 2

Asp Arg Xaa Tyr Ile His Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (4)..(4)
<223> OTHER INFORMATION: homoserine

<400> SEQUENCE: 3

Asp Arg Val Xaa Ile His Cys
1               5

<210> SEQ ID NO 4
<211> LENGTH: 12
<212> TYPE: PRT
<213> ORGANISM: Artificial Sequence
<220> FEATURE:
<223> OTHER INFORMATION: Chemically synthesized peptide

<400> SEQUENCE: 4

Asp Arg Val Tyr Ile His Pro Phe His Leu Val Ile
1               5                   10
```

```
<210> SEQ ID NO 5
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Any amino acid or dicarboxylic acid; Asp, Glu,
      Asn, Acpc (1-aminocyclopentane carboxylic acid), Ala, Me2Gly
      (N,N-dimethylglycine), Pro, Bet (betaine), Glu, Gly, Asp, Sar
      (sarcosine) or Suc (succinic acid)
<220> FEATURE:
<221> NAME/KEY: MISC_FEATURE
<222> LOCATION: (2)..(2)
<223> OTHER INFORMATION: Arg, Lys, Ala, Cit (citrulline), Orn
      (ornithine), acetylated Ser, Sar, D-Arg or D-Lys
<220> FEATURE:
<221> NAME/KEY: MISC_FEATURE
<222> LOCATION: (3)..(3)
<223> OTHER INFORMATION: Val, Ala, Leu, Nle (norleucine), Ile, Gly, Lys,
      Pro, HydroxyPro (hydroxyproline), Aib (2-aminoisobutyric acid),
      Acpc or Tyr
<220> FEATURE:
<221> NAME/KEY: MISC_FEATURE
<222> LOCATION: (4)..(4)
<223> OTHER INFORMATION: Tyr, Tyr(PO3), Thr, Ser, homoSer (homoserine),
      azaTyr (aza-alpha1-homo-L-tyrosine) or Ala
<220> FEATURE:
<221> NAME/KEY: MISC_FEATURE
<222> LOCATION: (5)..(5)
<223> OTHER INFORMATION: Ile, Ala, Leu, norLeu, Val or Gly
<220> FEATURE:
<221> NAME/KEY: MISC_FEATURE
<222> LOCATION: (6)..(6)
<223> OTHER INFORMATION: His, Arg or 6-NH2-Phe (6-aminophenylalaine)
<220> FEATURE:
<221> NAME/KEY: MISC_FEATURE
<222> LOCATION: (7)..(7)
<223> OTHER INFORMATION: Cys, Pro or Ala

<400> SEQUENCE: 5

Xaa Xaa Xaa Xaa Xaa Xaa Xaa
1               5

<210> SEQ ID NO 6
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 6

Asp Arg Val Ser Ile His Cys
1               5

<210> SEQ ID NO 7
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (4)..(4)
<223> OTHER INFORMATION: Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (7)..(7)
```

```
<223> OTHER INFORMATION: Pro or Cys

<400> SEQUENCE: 7

Asp Arg Val Xaa Ile His Xaa
1               5

<210> SEQ ID NO 8
<211> LENGTH: 10
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (7)..(7)
<223> OTHER INFORMATION: Pro or Cys

<400> SEQUENCE: 8

Asp Arg Xaa Xaa Ile His Xaa Phe His Leu
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (7)..(7)
<223> OTHER INFORMATION: Pro or Cys

<400> SEQUENCE: 9

Asp Arg Xaa Xaa Ile His Xaa Phe
1               5

<210> SEQ ID NO 10
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (2)..(2)
<223> OTHER INFORMATION: Nle
<220> FEATURE:
<221> NAME/KEY: MISC_FEATURE
<222> LOCATION: (2)..(6)
<223> OTHER INFORMATION: 2,6-cyclization including thioether cyclization
```

```
<220> FEATURE:
<221> NAME/KEY: MISC_FEATURE
<222> LOCATION: (3)..(3)
<223> OTHER INFORMATION: Tyr or Ser
<220> FEATURE:
<221> NAME/KEY: MISC_FEATURE
<222> LOCATION: (6)..(6)
<223> OTHER INFORMATION: Pro or Cys

<400> SEQUENCE: 10

Arg Xaa Xaa Ile His Xaa Phe
1               5

<210> SEQ ID NO 11
<211> LENGTH: 6
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Nle
<220> FEATURE:
<221> NAME/KEY: MISC_FEATURE
<222> LOCATION: (2)..(2)
<223> OTHER INFORMATION: Tyr or Ser
<220> FEATURE:
<221> NAME/KEY: MISC_FEATURE
<222> LOCATION: (2)..(5)
<223> OTHER INFORMATION: 2,5-cyclization including thioether cyclization
<220> FEATURE:
<221> NAME/KEY: MISC_FEATURE
<222> LOCATION: (5)..(5)
<223> OTHER INFORMATION: Pro or Cys

<400> SEQUENCE: 11

Xaa Xaa Ile His Xaa Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (7)..(7)
<223> OTHER INFORMATION: Pro or Cys

<400> SEQUENCE: 12

Asp Arg Xaa Xaa Ile His Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: Chemically synthesized peptide
<220> FEATURE:
```

-continued

```
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (7)..(7)
<223> OTHER INFORMATION: Pro or Cys

<400> SEQUENCE: 13

Asp Arg Xaa Xaa Ile His Xaa Phe His
1               5

<210> SEQ ID NO 14
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Any amino acid, but typically a negatively-
      charged amino acid such as Glu or Asp
<220> FEATURE:
<221> NAME/KEY: MISC_FEATURE
<222> LOCATION: (2)..(2)
<223> OTHER INFORMATION: Any positively-charged amino acid such as Arg
      or Lys
<220> FEATURE:
<221> NAME/KEY: MISC_FEATURE
<222> LOCATION: (3)..(3)
<223> OTHER INFORMATION: Any aliphatic amino acid, such as Leu, Ile or
      Val
<220> FEATURE:
<221> NAME/KEY: MISC_FEATURE
<222> LOCATION: (4)..(4)
<223> OTHER INFORMATION: D-stereoisomer or L-stereoisomer
<220> FEATURE:
<221> NAME/KEY: MISC_FEATURE
<222> LOCATION: (4)..(4)
<223> OTHER INFORMATION: Abu (2-aminobutyric acid), Ala, Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (5)..(5)
<223> OTHER INFORMATION: Any aliphatic amino acid, such as Leu, Ile or
      Val
<220> FEATURE:
<221> NAME/KEY: MISC_FEATURE
<222> LOCATION: (6)..(6)
<223> OTHER INFORMATION: His
<220> FEATURE:
<221> NAME/KEY: MISC_FEATURE
<222> LOCATION: (6)..(6)
<223> OTHER INFORMATION: His
<220> FEATURE:
<221> NAME/KEY: MISC_FEATURE
<222> LOCATION: (7)..(7)
<223> OTHER INFORMATION: D-stereoisomer or L-stereoisomer
<220> FEATURE:
<221> NAME/KEY: MISC_FEATURE
<222> LOCATION: (7)..(7)
<223> OTHER INFORMATION: Abu (2-aminobutyric acid), Ala, Pro or Cys

<400> SEQUENCE: 14

Xaa Xaa Xaa Xaa Xaa Xaa Xaa
```

```
1               5

<210> SEQ ID NO 15
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (4)..(4)
<223> OTHER INFORMATION: Abu (2-aminobutyric acid)

<400> SEQUENCE: 15

Asp Arg Val Xaa Ile His Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Chemically synthesized peptide

<400> SEQUENCE: 16

Asp Arg Val Ala Ile His Ala
1               5

<210> SEQ ID NO 17
<211> LENGTH: 10
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Any amino acid, but typically a negatively
      charged amino acid such as Glu or Asp
<220> FEATURE:
<221> NAME/KEY: MISC_FEATURE
<222> LOCATION: (2)..(2)
<223> OTHER INFORMATION: Any positively charged amino acid such as Arg
      or Lys
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: D-stereoisomer or L-stereoisomer
<220> FEATURE:
<221> NAME/KEY: MISC_FEATURE
<222> LOCATION: (4)..(4)
<223> OTHER INFORMATION: Abu (2-aminobutyric acid), Ala, Tyr or Ser
<220> FEATURE:
<221> NAME/KEY: MISC_FEATURE
<222> LOCATION: (4)..(7)
<223> OTHER INFORMATION: 4,7-cyclization including thioether cyclization
<220> FEATURE:
<221> NAME/KEY: MISC_FEATURE
<222> LOCATION: (5)..(5)
<223> OTHER INFORMATION: Any aliphatic amino acid, such as Leu, Nle, Ile
      or Val
<220> FEATURE:
<221> NAME/KEY: MISC_FEATURE
<222> LOCATION: (6)..(6)
<223> OTHER INFORMATION: His
<220> FEATURE:
<221> NAME/KEY: MISC_FEATURE
<222> LOCATION: (7)..(7)
<223> OTHER INFORMATION: D-stereoisomer or L-stereoisomer
<220> FEATURE:
<221> NAME/KEY: MISC_FEATURE
```

```
<222> LOCATION: (7)..(7)
<223> OTHER INFORMATION: Abu (2-aminobutyric acid), Ala, Pro or Cys
<220> FEATURE:
<221> NAME/KEY: MISC_FEATURE
<222> LOCATION: (8)..(8)
<223> OTHER INFORMATION: Any amino acid other than Pro, typically Phe or
      Ile
<220> FEATURE:
<221> NAME/KEY: MISC_FEATURE
<222> LOCATION: (9)..(9)
<223> OTHER INFORMATION: His
<220> FEATURE:
<221> NAME/KEY: MISC_FEATURE
<222> LOCATION: (10)..(10)
<223> OTHER INFORMATION: Any aliphatic residue, such as Ile, Val or Leu

<400> SEQUENCE: 17

Xaa Xaa Xaa Xaa Xaa Xaa Xaa Xaa Xaa Xaa
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Abu (2-aminobutyric acid)

<400> SEQUENCE: 18

Asp Arg Xaa Xaa Ile His Ala
1               5

<210> SEQ ID NO 19
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle

<400> SEQUENCE: 19

Asp Arg Xaa Ala Ile His Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle
<220> FEATURE:
<221> NAME/KEY: MISC_FEATURE
<222> LOCATION: (4)..(4)
<223> OTHER INFORMATION: Abu (2-aminobutyric acid)

<400> SEQUENCE: 20

Asp Arg Xaa Xaa Ile His Ala Ile
1               5
```

```
<210> SEQ ID NO 21
<211> LENGTH: 8
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (3)..(3)
<223> OTHER INFORMATION: Nle

<400> SEQUENCE: 21

Asp Arg Xaa Ala Ile His Ala Ile
1               5

<210> SEQ ID NO 22
<211> LENGTH: 7
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (4)..(7)
<223> OTHER INFORMATION: 4,7-cyclization including thioether cyclization

<400> SEQUENCE: 22

Asp Arg Val Ser Ile His Cys
1               5
```

COMPOSITIONS AND METHODS FOR TREATMENT OF DIABETES

CROSS-REFERENCE TO RELATED APPLICATIONS

This application claims priority from U.S. Provisional Patent Application Ser. No. 61/660,888, filed on Jun. 18, 2012, and U.S. Provisional Patent Application Ser. No. 61/720,296, filed on Oct. 30, 2012, the disclosures of which are hereby incorporated in their entirety.

SEQUENCE LISTING

The present specification makes reference to a Sequence Listing submitted electronically as an ASCII .txt file named "Sequence Listing" on Feb. 1, 2013. The .txt file was generated on Jan. 30, 2013 and is 11 KB in size. The entire contents of the Sequence Listing are herein incorporated by reference.

BACKGROUND

Diabetes is a disease characterized by increases in blood glucose levels caused by an inability to properly produce or respond to insulin. Diabetes is the seventh leading cause of death in the United States and is a leading cause of kidney failure, nontraumatic lower-limb amputations, blindness, heart disease and stroke. In 2010, there were 18.8 million diagnosed cases of diabetes and an estimated 7 million undiagnosed cases in the United States alone (National Diabetes Information Clearinghouse, National Institute of Diabetes and Digestive and Kidney Diseases (NIDDK), National Institutes of Health (NIH)).

SUMMARY OF THE INVENTION

The present invention provides, among other things, improved methods for treating or preventing Diabetes, in particular, based on the use of an angiotensin (1-7) peptide, including both linear and cyclic peptides, functional equivalents, analogs or derivatives thereof and/or a non-peptidic Angiotensin-(1-7) receptor agonist. As described in the Examples section below, the present invention is, in part, based on the surprising discovery that treatment with an angiotensin (1-7) peptide significantly reduced blood glucose levels in a diabetic mouse model. Prior to the present invention, conflicting evidence existed with respect to the possible interaction between the renin-angiotensin system (RAS) and the metabolic pathways regulating Diabetes. On one hand, it was reported that Angiotensin-converting enzyme 2 (ACE2) is localized to the pancreas and may play a role in glucose homeostasis. Fang H. J. and Yang J. K., *J. Inter. Med. Res.* 2010; 38:558-569. On the other hand, administration of an angiotensin-(1-7) receptor agonist AVE0991 in a mouse model had no effect on blood glucose level. Ebermann L. et al. *Eur. J. Pharm.*, 590 (2008) 276-280 Ebermann L. et al. *Eur. J. Pharm.*, 590 (2008) 276-280. No one has shown that Ang-(1-7) itself or particular non-peptidic Ang-(1-7) receptor agonist can positively affect blood glucose levels. Therefore, the present invention represents a novel treatment for Diabetes.

In some embodiments, the present invention provides methods of treating diabetes comprising administering to a subject who is suffering from or susceptible to diabetes an angiotensin (1-7) peptide and/or a non-peptidic Angiotensin-(1-7) receptor agonist. In some embodiments, the angiotensin (1-7) peptide and/or a non-peptidic Angiotensin-(1-7) receptor agonist is administered at an effective dose periodically at an administration interval such that at least one symptom or feature of diabetes is reduced in intensity, severity, duration, or frequency or has delayed in onset. In some embodiments, the diabetes is type 1 diabetes. In some embodiments, the diabetes is type 2 diabetes. In some embodiments, the diabetes is gestational diabetes. In some embodiments, the subject is suffering from pre-diabetes.

In some embodiments, the angiotensin (1-7) peptide and/or a non-peptidic Angiotensin-(1-7) receptor agonist is administered daily, twice a week, weekly, once every two weeks, once every three weeks, monthly, or at a variable interval. In some embodiments, the angiotensin (1-7) peptide and/or a non-peptidic Angiotensin-(1-7) receptor agonist is administered intravenously, intradermally, orally, by inhalation, transdermally (topical), subcutaneously, and/or transmucosally.

In some embodiments, the angiotensin (1-7) peptide and/or a non-peptidic Angiotensin-(1-7) receptor agonist is administered at the effective dose ranging from about 1-1000 µg/kg/day (e.g., from about 1-900 µg/kg/day, from about 1-800 µg/kg/day, from about 1-700 µg/kg/day, from about 1-600 µg/kg/day, from about 1-500 µg/kg/day, from about 1-400 µg/kg/day, from about 1-300 µg/kg/day, from about 1-200 µg/kg/day, from about 1-100 µg/kg/day, from about 1-90 µg/kg/day, from about 1-80 µg/kg/day, from about 1-70 µg/kg/day, from about 1-60 µg/kg/day, from about 1-50 µg/kg/day, from about 1-40 µg/kg/day, from about 1-30 µg/kg/day, from about 1-20 µg/kg/day, or from about 1-10 µg/kg/day). In some embodiments, the angiotensin (1-7) peptide is administered at the effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 µg/kg/day. In some embodiments, the angiotensin (1-7) peptide and/or a non-peptidic Angiotensin-(1-7) receptor agonist is administered at the effective dose ranging from about 50-500 µg/kg/day.

In some embodiments, the administration of the angiotensin (1-7) peptide and/or a non-peptidic Angiotensin-(1-7) receptor agonist results in a 10%, 20%, 30%, 40%, 50%, 60%, 70%, 80%, 90% or 95% decrease in blood glucose in the subject as compared to a control (e.g., the blood glucose level in the subject prior to the treatment or the blood glucose level in a untreated subject). In some embodiments, the administration of the angiotensin (1-7) peptide and/or a non-peptidic Angiotensin-(1-7) receptor agonist results in a 10%, 20%, 30%, 40%, or 50% reduction in fasting blood glucose levels in the subject as compared to a control.

In some embodiments, the administration of the angiotensin (1-7) peptide and/or a non-peptidic Angiotensin-(1-7) receptor agonist reduces the blood glucose level in the subject to less than about 200 mg/dL (e.g., less than about 190 mg/dL, less than about 180 mg/dL, less than about 170 mg/dL, less than about 160 mg/dL, less than about 150 mg/dL, or less than about 140 mg/dL). In some embodiments, the administration of the angiotensin (1-7) peptide and/or a non-peptidic Angiotensin-(1-7) receptor agonist reduces the blood glucose level in the subject to within the normal range. In some embodiments, the glucose level is measured by a glucose tolerance test. the glucose level is measured by a glucose tolerance test. In some embodiments, the decrease or reduction of the blood glucose is archived within about 2 weeks of treatment (e.g., within about 3, 4, 5, 6, 7, 8, 9, or 10 weeks of treatment). In some embodiments, the decrease or reduction of the blood glucose is archived within about 1 month of treatment (e.g., within about 2, 3, 4, 5, 6, 7, 8, 9, 10, 11, or 12 months of treatment).

In some embodiments, the administration of an angiotensin (1-7) peptide and/or a non-peptidic Angiotensin-(1-7) receptor agonist reduces the fasting glucose level in the subject to less than 130 mg/dL. In some embodiments, the administration of an angiotensin (1-7) peptide and/or a non-peptidic Angiotensin-(1-7) receptor agonist reduces the fasting glucose level in the subject to less than 125 mg/dL. In some embodiments, the administration of an angiotensin (1-7) peptide and/or a non-peptidic Angiotensin-(1-7) receptor agonist reduces the fasting glucose level in the subject to less than 120 mg/dL. In some embodiments, the administration of an angiotensin (1-7) peptide and/or a non-peptidic Angiotensin-(1-7) receptor agonist reduces the fasting glucose level in the subject to less than 115 mg/dL. In some embodiments, the administration of an angiotensin (1-7) peptide and/or a non-peptidic Angiotensin-(1-7) receptor agonist reduces the fasting glucose level in the subject to less than 110 mg/dL. In some embodiments, the administration of an angiotensin (1-7) peptide and/or a non-peptidic Angiotensin-(1-7) receptor agonist reduces the fasting glucose level in the subject to less than 105 mg/dL. In some embodiments, the administration of an angiotensin (1-7) peptide and/or a non-peptidic Angiotensin-(1-7) receptor agonist reduces the fasting glucose level in the subject to less than 100 mg/dL.

In some embodiments, the angiotensin (1-7) peptide and/or a non-peptidic Angiotensin-(1-7) receptor agonist is administered in combination with an anti-diabetic medication. In some embodiments, a suitable anti-diabetic medication is selected from the group consisting of biguanides such as Metformin, Buformin and Phenformin, thiazolidinediones's (PPAR) such as Pioglitazone, Rivoglitazone, Rosiglitazone and Troglitazone, dual PPAR agonists such as Aleglitazar, Muraglitazar and Tesaglitazar, or secretagogues including sulphonylureas such as Carbutamide, Chloropropamide, Gliclazide, Tolbutamide, Tolazamide, Glipizide, Glibenclamide, Glyburide, Gliquidone, Glyclopyramide and Glimepriride, Meglitinides/glinides (K+) such as Nateglinide, Repaglinide and Mitiglinide, incretin mimetics including GLP-1 analogs such as Exenatide, Liraglutide and Albiglutide, DPP-4 inhibitors such as Alogliptin, Linagliptin, Saxagliptin, Sitagliptin and Vildagliptin, insulin, insulin analogs or special formulations such as (fast acting) Insulin lispro, Insulin aspart, Insulin glulisine, (long acting) Insulin glargine, Insulin detemir), inhalable insulin—Exubra and NPH insulin, and others including alpha-glucosidase inhibitors such as Acarbose, Miglitol and Voglibose, amylin or amylin analogues such as Pramlintide, SGLT2 inhibitors such as Dapagliflozin, Remogliflozin and Sergliflozin as well as miscellaneous ones including Benfluorex and Tolrestat, or combinations thereof.

In some embodiments, the angiotensin (1-7) peptide comprises the naturally-occurring Angiotensin (1-7) amino acid sequence of $Asp^1$-$Arg^2$-$Val^3$-$Tyr^4$-$Ile^5$-$His^6$-$Pro^7$ (SEQ ID NO:1). In other embodiments, the angiotensin (1-7) peptide and/or a non-peptidic Angiotensin-(1-7) receptor agonist is a functional equivalent of SEQ ID NO:1. In some embodiments, the functional equivalent is a linear peptide. In some embodiments, the linear peptide comprises a sequence that includes at least four amino acids from the seven amino acids that appear in the naturally-occurring Angiotensin (1-7), wherein the at least four amino acids maintain their relative positions as they appear in the naturally-occurring Angiotensin (1-7). In some embodiments, the linear peptide comprises a sequence that includes at least five amino acids from the seven amino acids that appear in the naturally-occurring Angiotensin (1-7), wherein the at least five amino acids maintain their relative positions as they appear in the naturally-occurring Angiotensin (1-7). In some embodiments, the linear peptide comprises a sequence that includes at least six amino acids from the seven amino acids that appear in the naturally-occurring Angiotensin (1-7), wherein the at least six amino acids maintain their relative positions as they appear in the naturally-occurring Angiotensin (1-7). In some embodiments, the at least four, five or six amino acids, respectively, further maintain their relative spacing as they appear in the naturally-occurring Angiotensin (1-7).

In some embodiments, the linear peptide contains 4-25 (e.g., 4-20, 4-15, 4-12, 4-10, 4-9, 4-8, 4-7, or 4-6 amino acids). In some embodiments, the linear peptide is a fragment of the naturally-occurring Angiotensin (1-7). In some embodiments, the linear peptide contains amino acid substitutions, deletions and/or insertions in the naturally-occurring Angiotensin (1-7). In some embodiments, the linear peptide has an amino acid sequence of $Asp^1$-$Arg^2$-$Nle^3$-$Tyr^4$-$Ile^5$-$His^6$-$Pro^7$ (SEQ ID NO:2). In some embodiments, the linear peptide has an amino acid sequence of $Asp^1$-$Arg^2$-$Val^3$-$Ser^4$-$Ile^5$-$His^6$-$Cys^7$ (SEQ ID NO:6).

In some embodiments, the functional equivalent is a cyclic peptide. In some embodiments, the cyclic peptide comprises a linkage between amino acids. In some embodiments, the linkage is located at residues corresponding to positions $Tyr^4$ and $Pro^7$ in naturally-occurring Angiotensin (1-7). In some embodiments, the linkage is a thioether bridge. In some embodiments, the cyclic peptide comprises an amino acid sequence otherwise identical to the naturally-occurring Angiotensin (1-7) amino acid sequence of $Asp^1$-$Arg^2$-$Val^3$-$Tyr^4$-$Ile^5$-$His^6$-$Pro^7$ (SEQ ID NO:1). In some embodiments, the cyclic peptide comprises a norleucine (Nle) replacing position $Val^3$ in naturally-occurring Angiotensin (1-7). In some embodiments, the cyclic peptide is a 4,7-cyclized angiotensin (1-7) with the following formula:

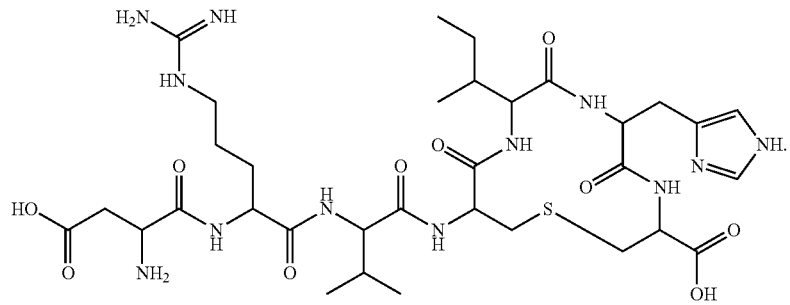 [SMILES: CCC(C)C1NC(=O)C(NC(=O)C(NC(=O)C(CCCNC(=N)N)NC(=O)C(N)CC(=O)O)C(C)C)CSCC(C(=O)O)NC(=O)C(Cc2c[nH]cn2)NC1=O]

In some embodiments, the angiotensin (1-7) peptide comprises one or more chemical modifications to increase protease resistance, serum stability and/or bioavailability. In some embodiments, the one or more chemical modifications comprise pegylation.

In some embodiments, the present invention provides methods of treating diabetes including administering to a subject who is suffering from or susceptible to diabetes an angiotensin (1-7) receptor agonist. In some embodiments, the angiotensin (1-7) receptor agonist is a non-peptidic agonist. In some embodiments, the non-peptidic agonist is a compound with the following structure:

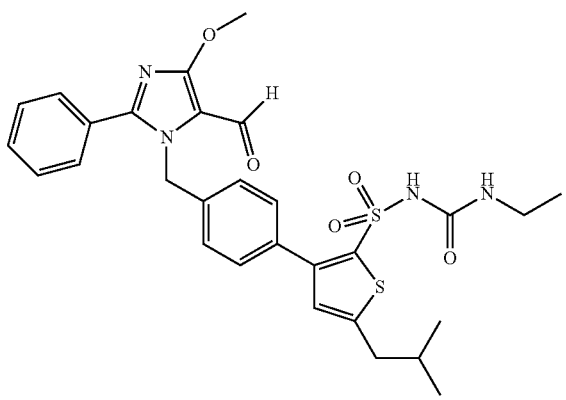 [SMILES: CCNC(=O)NS(=O)(=O)c1sc(CC(C)C)cc1-c1ccc(Cn2c(-c3ccccc3)nc(OC)c2C=O)cc1]

or a pharmaceutically acceptable salt thereof.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The figures are for illustration purposes only not for limitation.

DEFINITIONS

Figure 1:
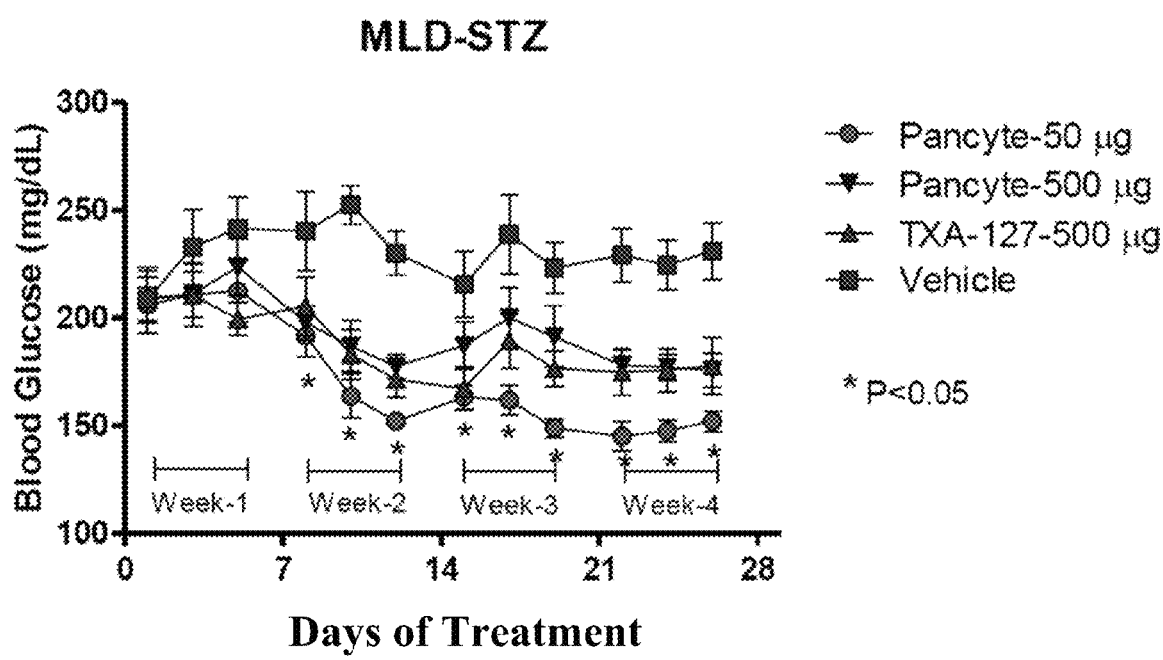
FIG. 1 shows an exemplary graph of blood glucose in mg/dL over 28 days plotted as a function of time in the streptozotocin (STZ) induced diabetic mouse model. STZ induced diabetic mice were dosed with PanCyte (SEQ ID NO:5) 50 and 500 µg/kg body weight, TXA-127 (SEQ ID NO:1) 500 µg/kg body weight, and one group was dosed with PBS as vehicle control.

In order for the present invention to be more readily understood, certain terms are first defined below. Additional definitions for the following terms and other terms are set forth throughout the specification.

Agonist: As used herein, the term "agonist" refers to any molecule that has a positive impact in a function of a protein of interest. In some embodiments, an agonist directly or indirectly enhances, strengthens, activates and/or increases an activity of a protein of interest. In particular embodiments, an agonist directly interacts with the protein of interest. Such agonists can be, e.g., proteins, chemical compounds, small molecules, nucleic acids, antibodies, drugs, ligands, or other agents.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In certain embodiments, a peptide has no intrinsic biological activity but that inhibits the effects of one or more naturally-occurring angiotensin compounds is considered to be biologically active.

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Functional equivalent or derivative: As used herein, the term "functional equivalent" or "functional derivative" denotes a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of disease as the individual being treated, who is about the same age as the individual being treated (to ensure that the stages of the disease in the treated individual and the control individual(s) are comparable).

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Pre-Diabetes: As used herein, the term "pre-diabetes" refers to a condition or state in which some but not all of the symptoms, features or diagnostic criteria for diabetes are met. For example, in some pre-diabetes patients, the fasting blood glucose level is consistently elevated above what is considered normal levels, yet is not high enough to be diagnosed as diabetes. Thus, in some embodiments, pre-diabetes may also be known as "impaired fasting glucose."

Prevent: As used herein, the term "prevent" or "prevention", when used in connection with the occurrence of a disease, disorder, and/or condition, refers to reducing the risk of developing the disease, disorder and/or condition. See the definition of "risk."

Polypeptide: The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., Diabetes). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., Diabetes). In some embodiments a reference sample or group of reference samples are from individuals comparable to a particular individual. In some embodiments, relative risk is 0, 1, 2, 3, 4, 5, 6, 7, 8, 9, 10, or more.

Stability: As used herein, the term "stable" refers to the ability of the therapeutic agent to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In certain embodiments, pharmaceutical compositions described herein have been formulated such that they are capable of stabilizing, or alternatively slowing or preventing the degradation, of one or more therapeutic agents formulated therewith. In the context of a formulation a stable formulation is one in which the therapeutic agent therein essentially retains its physical and/or chemical integrity and biological activity upon storage and during processes (such as freeze/thaw, mechanical mixing and lyophilization).

Subject: As used herein, the term "subject" refers to a human or any non-human animal (e.g., mouse, rat, rabbit, dog, cat, cattle, swine, sheep, horse or primate). A human includes pre and post natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event (for example, Diabetes) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, improved compositions and methods for treating or reducing risk of diseases, disorders, or conditions that cause elevated blood sugar levels (i.e., diabetes) based on the use of angiotensin-(1-7) peptides or functional equivalents, analogs or derivatives thereof, or angiotensin (1-7) receptor agonists such as the non-peptidic Ang-(1-7) receptor agonist AVE 0991.

Various aspects of the invention are described in detail in the following sections. The use of sections is not meant to limit the invention. Each section can apply to any aspect of the invention. In this application, the use of "or" means "and/or" unless stated otherwise.

Blood Sugar and Metabolism

An Ang peptide (e.g., angiotensin-(1-7) peptide (or functional equivalent, analog or derivative thereof) or angiotensin (1-7) receptor agonist (e.g., AVE 0991) as described herein can be used for treating or reducing risk of diseases, disorders, or conditions that cause elevated blood sugar levels. Such conditions include, but are not limited to diabetes, pre-diabetes, and/or metabolic syndrome.

The blood sugar concentration in the blood in healthy individuals is normally maintained between 64.8 and 104.4 mg/dL (American Diabetes Association, "Standards of Medical Care in Diabetes—2010", *Diabetes Care,* 33: S1-S61, 2010). The body tightly regulates blood sugar levels as part of metabolic homeostasis. Blood sugar levels fluctuate throughout the day, and are usually lowest in the morning, before the first meal of the day, and rise for an hour or two after meals.

Glucose is the primary source of sugar in the blood and is the primary source of energy for the body's cells. The hormone insulin, which is produced in the beta cells in the islets of Langerhans in the pancreas, allows cells of the body to take up glucose from the blood and store it as glycogen.

Many clinical methods exist for assaying blood sugar levels, including but not limited to, fasting blood sugar test, urine glucose test, two-hour postprandial blood sugar test, oral glucose tolerance test, intravenous glucose tolerance test, glycosylated hemoglobin test, self-monitoring of glucose levels via patient testing, and/or random blood sugar testing. The fasting blood sugar/blood glucose test is the most common test for initial assessment of the presence or risk for developing diabetes. The test requires that an individual abstains from eating for at least 8 hours prior to the test. Typically, up to 100 mg/dL is considered normal for a fasting blood glucose test. Subjects with levels between 100 mg/dL and 125 mg/dL are typically considered to have impaired fasting glucose, or be pre-diabetic, and subjects with levels that are 126 mg/dL or greater are typically considered diabetic.

Typically, a glucose tolerance test is used for measuring blood sugar levels. Impaired glucose tolerance is generally diagnosed if the blood glucose level measured during a glucose tolerance test is in the range of 140 mg/dL (7.84 mM) to 199 mg/dL (11.1 mM). Diabetes is generally diagnosed if the measured blood glucose level is 200 mg/dL (11.2 mM) or higher. But, as physiological status fluctuates continually, no single glucose tolerance test is definitive, and treatment for reducing of blood glucose levels need not be predicated solely on the results of such testing.

Diabetes

An Ang peptide (e.g., an ang-(1-7) peptide or functional equivalent, analog or derivative thereof) or angiotensin (1-7) receptor agonist as described herein can be used for treating or reducing risk of Diabetes. Diabetes is well known in the art (American Diabetes Association, "Standards of Medical Care in Diabetes—2010", *Diabetes Care*, 33: S1-S61, 2010). Diabetes is a disease in which the body does not produce or respond to insulin correctly. The inability to produce or respond to insulin correctly characteristic of diabetes results in elevated blood sugar levels.

There are two major types of diabetes. Type 1 diabetes is an auto-immune disease that affects the islets of Langerhans, destroying the body's ability to produce insulin. Type I diabetes represents 10% of all diabetes cases and affects as many as 1 million people in the United States. Type 2 diabetes is a metabolic disorder resulting from the body's inability to produce enough insulin or properly use the insulin produced. Roughly 90% of all diabetic individuals in the United States suffer from Type 2 diabetes. Other, less common forms of diabetes include gestational diabetes, in which pregnant women, who have never had diabetes before, have a high blood glucose level during pregnancy, monogenic diabetes, which behaves similarly to Type 1 diabetes and is caused by a single gene mutation, congenital diabetes, which is due to genetic defects of insulin secretion, cystic fibrosis-related diabetes, and steroid diabetes induced by high doses of glucocorticoids.

In some embodiments, an Ang peptide or angiotensin (1-7) receptor agonist as described herein can be used for treating Diabetes. Diabetes can be associated with a wide range of conditions and complications affecting various organs throughout the body and can severely compromise quality of life and can even be fatal. Therefore, there is a need in the art for effective means of treating and preventing the development and progression of diabetes and associated complications.

Elevated blood sugar levels are responsible for most of the symptoms associated with diabetes. Diabetes associated symptoms include, but are not limited to polyuria (frequent urination), polydipsia (increased thirst), polyphagia (increased hunger). Prolonged high blood glucose can cause glucose absorption in the lens of the eye, which leads to changes in its shape, resulting in vision changes. A number of skin rashes which can occur in diabetes are collectively known as diabetic dermadromes. Long term complications of diabetes include damage to the blood vessels. Diabetes doubles the risk of cardiovascular disease. The main "macrovascular" diseases (related to atherosclerosis of larger arteries) are ischemic heart disease (angina and myocardial infarction), stroke and peripheral vascular disease. Diabetes also causes "microvascular" complications—damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems (such as diabetic foot ulcers) that can be difficult to treat and occasionally require amputation.

In some embodiments, an Ang peptide or angiotensin (1-7) receptor agonist as described herein can be used for reducing risk of Diabetes. Risk factors associated with diabetes in general, and with the development of Type 2 diabetes in particular, include a family history of diabetes, belonging to certain ethnic or racial groups, a history of gestational diabetes, obesity, in particular, high levels of visceral or abdominal fat, a sedentary lifestyle, age, high blood pressure, schizophrenia, as well as altered glucose metabolism, including impaired glucose tolerance (IGT) or prediabetes. Therefore, there is a need in the art for effective means of treating and preventing the development and progression of risk factors associated with diabetes.

Anti-diabetics traditionally used to treat Diabetes include insulin sensitizers including biguanides such as Metformin, Buformin and Phenformin, TZD's (PPAR) such as Pioglitazone, Rivoglitazone, Rosiglitazone and Troglitazone, dual PPAR agonists such as Aleglitazar, Muraglitazar and Tesaglitazar, or secretagogues including sulphonylureas such as Carbutamide, Chloropropamide, Gliclazide, Tolbutamide, Tolazamide, Glipizide, Glibenclamide, Glyburide, Gliquidone, Glyclopyramide and Glimepriride, Meglitinides/glinides (K+) such as Nateglinide, Repaglinide and Mitiglinide, GLP-1 analogs such as Exenatide, Liraglutide and Albiglutide, DPP-4 inhibitors such as Alogliptin, Linagliptin, Saxagliptin, Sitagliptin and Vildagliptin, insulin analogs or special formulations such as (fast acting) Insulin lispro, Insulin aspart, Insulin glulisine, (long acting) Insulin glargine, Insulin detemir), inhalable insulin—Exubra and NPH insulin, and others including alpha-glucosidase inhibitors such as Acarbose, Miglitol and Voglibose, amylin analogues such as Pramlintide, SGLT2 inhibitors such as Dapagliflozin, Remogliflozin and Sergliflozin as well as miscellaneous ones including Benfluorex and Tolrestat.

Insulin is the primary treatment for Type 1 diabetes and its use as a treatment for Type 2 diabetes is becoming more prevalent. Insulin is administered through a course of injections that need to be administered in a carefully scheduled fashion, often requiring daily or even multiple daily injections. Treatments requiring injections of insulin carry with them associated risks of hypoglycemia and hyperinsulinemia. Further, the success of such treatments is often compromised by lack of patient compliance, i.e., failure to follow the recommended treatment schedule. There is a need for courses of treatment that have improved ease of administration, increasing patient comfort as well as the likelihood of patient compliance.

Treatment of Diabetes with Ang (1-7)

There are several lines of evidence suggesting that there is overlap between the renin-angiotensin system (RAS) and the metabolic pathways regulating Diabetes. However, the exact nature of the interaction remains to be determined (Bathe, D. et al., "ACE2 and Diabetes: ACE of ACEs?", 59: 2994-2996, 2010).

Angiotensin converting enzyme 2 (ACE2) is a component of RAS and is involved in Ang-(1-7) generation. ACE2 has been shown to be localized to the pancreas of rats (Fang, H. J. et al., "Tissue-specific Pattern of Angiotensin converting Enzyme 2 Expression in Rat" Journal of Int. Med. Res., 38: 558-569, 2010). Additionally, when ACE2 is expressed in a diabetic mouse model, a decrease in blood glucose and an increase in insulin levels is seen (Bindom, S. M. et al., "Angiotensin I—Converting Enzyme Type 2 (ACE2) Gene Therapy Improves Glycemic Control in Diabetic Mice", 59: 2540-2548, 2010).

Ang-(1-7) signals through the Mas receptor, another component of RAS. Mice lacking the Mas receptor have higher insulin resistance and glycemia (Published International Application No. WO 2007/121546). In the diabetic mouse model described above, administration of the Mas receptor antagonist D-Ala$^7$-Ang-(1-7) blocked the decrease in blood glucose and an increase in insulin levels is seen with ACE2 expression.

Administration of Ang-(1-7) to directly to adipocytes in vitro resulted in increased glucose uptake (Liu, C. et al, "Angiotensin-(1-7) suppresses oxidative stress and improves glucose uptake via Mas receptor in adipocytes", ACTA Diabetologica, 2011, 49(4):291-299).

The present invention provides, among other things, methods and compositions for diseases, disorders, or conditions that cause elevated blood sugar levels (i.e., Diabetes), it is meant that the compositions of the present invention may affect one or more aspects of diseases, disorders, or conditions that cause elevated blood sugar levels, including decreasing resultant symptoms. For example, treatment with an Ang peptide or angiotensin (1-7) receptor agonist as described herein can reduce the severity of Diabetes, such as by reducing blood glucose levels. In one embodiment, treatment with an Ang peptide or angiotensin (1-7) receptor agonist as described herein reduces Diabetes by 40% as compared to a control. In some embodiments, treatment with an Ang peptide or angiotensin (1-7) receptor agonist results in the subject being substantially free of Diabetes following treatment. The present invention may be used as a monotherapy or as part of a combination therapy with one or more other prophylactic or therapeutic materials routinely used to treat or reduce risk of Diabetes.

In some embodiments, the present invention comprises a method of treating or reducing the risk of Diabetes by administering to a subject who is suffering from or susceptible to Diabetes an Ang peptide or angiotensin (1-7) receptor agonist, such as a non-peptidic angiotensin (1-7) receptor agonist, as described herein.

In some embodiments, a subject is any multicellular organism. In some embodiments, a subject is a mouse, rat, dog, non-human primate or other animal commonly used for laboratory experiments. In some embodiments, a subject is an individual. In some embodiments, an individual is a human. In some embodiments, a subject has or is susceptible to a disease, disorder, or condition. In some embodiments, a subject has or is susceptible to Diabetes. In some embodiments a subject who is susceptible to Diabetes comprises a subject with impaired glucose tolerance.

In some embodiments, an Ang peptide or angiotensin (1-7) receptor agonist as described herein is administered to a subject having or at risk of Diabetes at an effective dose periodically at an administration interval such that at least one symptom or feature of Diabetes is reduced in intensity, severity, duration, or frequency or has delayed in onset.

Angiotensin (1-7) Peptides

As used herein, the term "angiotensin (1-7) peptide" refers to both naturally-occurring Angiotensin (1-7) and any functional equivalent, analogue or derivative of naturally-occurring Angiotensin (1-7). As used herein, "peptide" and "polypeptide" are interchangeable terms and refer to two or more amino acids bound together by a peptide bond. As used herein, the terms "peptide" and "polypeptide" include both linear and cyclic peptide. The terms "angiotensin-(1-7)", "Angiotensin-(1-7)", "Ang-(1-7)", and "TXA-127" are used interchangeably.

Naturally-Occurring Angiotensin (1-7)

Naturally-occurring Angiotensin (1-7) (also referred to as Ang-(1-7)) is a seven amino acid peptide shown below:

$$\text{Asp}^1\text{-Arg}^2\text{-Val}^3\text{-Tyr}^°\text{-Ile}^5\text{-His}^6\text{-Pro}^7 \quad \text{(SEQ ID NO:1)}$$

It is part of the renin-angiotensin system and is converted from a precursor, also known as Angiotensinogen, which is an α-2-globulin that is produced constitutively and released into the circulation mainly by the liver. Angiotensinogen is a member of the serpin family and also known as renin substrate. Human angiotensinogen is 452 amino acids long, but other species have angiotensinogen of varying sizes. Typically, the first 12 amino acids are the most important for angiotensin activity:

$$\text{Asp}^1\text{-Arg}^2\text{-Val}^3\text{-Tyr}^4\text{-Ile}^5\text{-His}^6\text{-Pro}^7\text{-Phe}^8\text{-His}^9\text{-Leu}^{10}\text{-Val}^{11}\text{-Ile}^{12} \quad \text{(SEQ ID NO:4)}$$

Different types of angiotensin may be formed by the action of various enzymes. For example, Angiotensin (1-7) is generated by action of Angiotensin-converting enzyme 2 (ACE 2).

Ang-(1-7) is an endogenous ligand for Mas receptors. Mas receptors are G-protein coupled receptor containing seven transmembrane spanning regions. As used herein, the term "angiotensin-(1-7) receptor" encompasses the G Protein-Coupled Mas Receptors.

As used herein, the term "naturally-occurring Angiotensin (1-7)" includes any Angiotensin (1-7) peptide purified from natural sources and any recombinantly produced or chemically synthesized peptides that have an amino acid sequence identical to that of the naturally-occurring Angiotensin (1-7).

Functional Equivalents, Analogs or Derivatives of Ang-(1-7)

In some embodiments, an angiotensin (1-7) peptide suitable for the present invention is a functional equivalent of naturally-occurring Ang-(1-7). As used herein, a functional equivalent of naturally-occurring Ang-(1-7) refers to any peptide that shares amino acid sequence identity to the naturally-occurring Ang-(1-7) and retain substantially the same or similar activity as the naturally-occurring Ang-(1-7). For example, in some embodiments, a functional equivalent of naturally-occurring Ang-(1-7) described herein has pro-angiogenic activity as determined using methods described herein or known in the art, or an activity such as nitric oxide release, vasodilation, improved endothelial function, antidiuresis, or one of the other properties discussed herein, that positively impacts angiogenesis. In some embodiments, a functional equivalent of naturally-occurring Ang-(1-7) described herein can bind to or activate an angiotensin-(1-7) receptor (e.g., the G protein-coupled Mas receptor) as determined using various assays described herein or known in the art. In some embodiments, a functional equivalent of Ang-(1-7) is also referred to as an angiotensin (1-7) analogue or derivative, or functional derivative.

Typically, a functional equivalent of angiotensin (1-7) shares amino acid sequence similarity to the naturally-occurring Ang-(1-7). In some embodiments, a functional equivalent of Ang-(1-7) according to the invention contains a sequence that includes at least 3 (e.g., at least 4, at least 5, at least 6, at least 7) amino acids from the seven amino acids that appear in the naturally-occurring Ang-(1-7), wherein the at least 3 (e.g., at least 4, at least 5, at least 6, or at least 7) amino acids maintain their relative positions and/or spacing as they appear in the naturally-occurring Ang-(1-7).

In some embodiments, a functional equivalent of Ang-(1-7) also encompasses any peptide that contains a sequence at least 50% (e.g., at least 60%, 70%, 80%, or 90%) identical to the amino acid sequence of naturally-occurring Ang-(1-7). Percentage of amino acid sequence identity can be determined by alignment of amino acid sequences. Alignment of amino acid sequences can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology* 266, 460-480 (1996); http://blast.wustl/edu/ blast/README.html). WU-BLAST-2 uses several search parameters, most of which are set to the default values. The adjustable parameters are set with the following values: overlap span=1, overlap fraction=0.125, word threshold (T)=11. HSP score (S) and HSP S2 parameters are dynamic values and are established by the program itself, depending upon the composition of the particular sequence, however, the minimum values may be adjusted and are set as indicated above.

In some embodiments, a functional equivalent, analogue or derivative of Ang-(1-7) is a fragment of the naturally-occurring Ang-(1-7). In some embodiments, a functional equivalent, analogue or derivative of Ang-(1-7) contains amino acid substitutions, deletions and/or insertions in the naturally-occurring Ang-(1-7). Ang-(1-7) functional equivalents, analogues or derivatives can be made by altering the amino acid sequences by substitutions, additions, and/or deletions. For example, one or more amino acid residues within the sequence of the naturally-occurring Ang-(1-7) (SEQ ID NO:1) can be substituted by another amino acid of a similar polarity, which acts as a functional equivalent, resulting in a silent alteration. Substitution for an amino acid within the sequence may be selected from other members of the class to which the amino acid belongs. For example, the positively charged (basic) amino acids include arginine, lysine, and histidine. The nonpolar (hydrophobic) amino acids include leucine, isoleucine, alanine, phenylalanine, valine, proline, tryptophan, and methionine. The uncharged polar amino acids include serine, threonine, cysteine, tyrosine, asparagine, and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions. For example, the amino acid sequence of a peptide inhibitor can be modified or substituted.

Examples of Ang-(1-7) functional equivalents, analogues and derivatives are described in the section entitled "Exemplary Angiotensin(1-7) Peptides" below.

An angiotensin-(1-7) peptide can be of any length. In some embodiments, an angiotensin-(1-7) peptide according to the present invention can contain, for example, from 5-25 amino acid residues, such as 5-20, 5-15 or 5-10 amino acid residues. In some embodiments, an Ang-(1-7) peptide according to the present invention contain 5, 6, 7, 8, 9, 10, 11, 12, 13, 14, 15, 16, 17, 18, 19, 20, 21, 22, 23, 24 or 25 residues.

In some embodiments, an angiotensin-(1-7) peptide contains one or more modifications to increase protease resistance, serum stability and/or bioavailability. In some embodiments, suitable modifications are selected from pegylation, acetylation, glycosylation, biotinylation, substitution with D-amino acid and/or un-natural amino acid, and/or cyclization of the peptide.

As used herein, the term "amino acid," in its broadest sense, refers to any compound and/or substance that can be incorporated into a polypeptide chain. In certain embodiments, an amino acid has the general structure $H_2N$—C(H) (R)—COOH. In certain embodiments, an amino acid is a naturally-occurring amino acid. In certain embodiments, an amino acid is a synthetic or un-natural amino acid (e.g., α,α-disubstituted amino acids, N-alkyl amino acids); in some embodiments, an amino acid is a D-amino acid; in certain embodiments, an amino acid is an L-amino acid. "Standard amino acid" refers to any of the twenty standard amino acids commonly found in naturally occurring peptides including both L- and D-amino acids which are both incorporated in peptides in nature. "Nonstandard" or "unconventional amino acid" refers to any amino acid, other than the standard amino acids, regardless of whether it is prepared synthetically or obtained from a natural source. As used herein, "synthetic or un-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical groups that can change the peptide's circulating half-life without adversely affecting its activity. Examples of unconventional or un-natural amino acids include, but are not limited to, citrulline, ornithine, norleucine, norvaline, 4-(E)-butenyl-4 (R)-methyl-N-methylthreonine (MeBmt), N-methyl-leucine (MeLeu), aminoisobutyric acid, statine, and N-methyl-alanine (MeAla). Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

In certain embodiments, angiotensin-(1-7) peptides contain one or more L-amino acids, D-amino acids, and/or un-natural amino acids.

In addition to peptides containing only naturally occurring amino acids, peptidomimetics or peptide analogs are also encompassed by the present invention. Peptide analogs are commonly used in the pharmaceutical industry as non-peptide drugs with properties analogous to those of the template peptide. The non-peptide compounds are termed "peptide mimetics" or peptidomimetics (Fauchere et al., *Infect. Immun.* 54:283-287 (1986); Evans et al., *J. Med. Chem.* 30:1229-1239 (1987)). Peptide mimetics that are structurally related to therapeutically useful peptides and may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —$CH_2NH$—, —$CH_2S$—, —$CH_2$—$CH_2$—, —CH=CH— (cis and trans), —$CH_2SO$—, —$CH(OH)CH_2$—, —$COCH_2$— etc., by methods well known in the art (Spatola, Peptide Backbone Modifications, Vega Data, 1(3):267 (1983); Spatola et al. *Life Sci.* 38:1243-1249 (1986); Hudson et al. *Int. J. Pept. Res.* 14:177-185 (1979); and Weinstein. B., 1983, Chemistry and Biochemistry, of Amino Acids, Peptides and Proteins, Weinstein eds, Marcel Dekker, New-York). Such peptide mimetics may have significant advantages over naturally-occurring polypeptides including more economical production, greater chemical stability, enhanced pharmacological properties (e.g., half-life, absorption, potency, efficiency, etc.), reduced antigenicity and others.

Ang-(1-7) peptides also include other types of peptide derivatives containing additional chemical moieties not normally part of the peptide, provided that the derivative retains the desired functional activity of the peptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives; and (6) derivatives conjugated to a polyethylene glycol (PEG) chain.

Ang-(1-7) peptides may be obtained by any method of peptide synthesis known to those skilled in the art, including synthetic (e.g., exclusive solid phase synthesis, partial solid phase synthesis, fragment condensation, classical solution synthesis, native-chemical ligation) and recombinant techniques. For example, the peptides or peptides derivatives can be obtained by solid phase peptide synthesis, which in brief, consist of coupling the carboxyl group of the C-terminal amino acid to a resin (e.g., benzhydrylamine resin, chloromethylated resin, hydroxymethyl resin) and successively adding N-alpha protected amino acids. The protecting groups may be any such groups known in the art. Before each new amino acid is added to the growing chain, the protecting group of the previous amino acid added to the chain is removed. Such solid phase synthesis has been disclosed, for example, by Merrifield, *J. Am. Chem. Soc.* 85: 2149 (1964); Vale et al., *Science* 213:1394-1397 (1981), in U.S. Pat. Nos. 4,305,872 and 4,316,891, Bodonsky et al. *Chem. Ind.* (London), 38:1597 (1966); and Pietta and Marshall, *Chem. Comm.* 650 (1970) by techniques reviewed in Lubell et al. "Peptides" Science of Synthesis 21.11, *Chemistry of Amides*. Thieme, Stuttgart, 713-809 (2005). The coupling of amino acids to appropriate resins is also well known in the art and has been disclosed in U.S. Pat. No. 4,244,946. (Reviewed in Houver-Weyl, *Methods of Organic Chemistry*. Vol E22a. Synthesis of Peptides and Peptidomimetics, Murray Goodman, Editor-in-Chief, Thieme. Stuttgart. New York 2002).

Unless defined otherwise, the scientific and technological terms and nomenclature used herein have the same meaning as commonly understood by a person of ordinary skill to which this invention pertains. Generally, the procedures of cell cultures, infection, molecular biology methods and the like are common methods used in the art. Such standard techniques can be found in reference manuals such as, for example, Ausubel et al., *Current Protocols in Molecular Biology*, Wiley Interscience, New York, 2001; and Sambrook et al., *Molecular Cloning: A Laboratory Manual*, 3$^{rd}$ edition, Cold Spring Harbor Laboratory Press, N.Y., 2001.

During any process of the preparation of an Ang-(1-7) peptide, it may be desirable to protect sensitive reactive groups on any of the molecule concerned. This may be achieved by means of conventional protecting groups such as those described in Protective Groups In Organic Synthesis by T. W. Greene & P. G. M. Wuts, 1991, John Wiley and Sons, New-York; and Peptides: chemistry and Biology by Sewald and Jakubke, 2002, Wiley-VCH, Wheinheim p. 142. For example, alpha amino protecting groups include acyl type protecting groups (e.g., trifluoroacetyl, formyl, acetyl), aliphatic urethane protecting groups (e.g., t-butyloxycarbonyl (BOC), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl). The amino acids side chain protecting groups include benzyl (for Thr and Ser), Cbz (Tyr, Thr, Ser, Arg, Lys), methyl ethyl, cyclohexyl (Asp, His), Boc (Arg, His, Cys) etc. The protecting groups may be removed at a convenient subsequent stage using methods known in the art.

Further, Ang-(1-7) peptides may be synthesized according to the FMOC protocol in an organic phase with protective groups. Desirably, the peptides are purified with a yield of 70% with high-pressure liquid chromatography (HPLC) on a C18 chromatography column and eluted with an acetonitrile gradient of 10-60%. The molecular weight of a peptide can be verified by mass spectrometry (reviewed in Fields, G. B. "Solid-Phase Peptide Synthesis" *Methods in Enzymology*. Vol. 289, Academic Press, 1997).

Alternatively, Ang-(1-7) peptides may be prepared in recombinant systems using, for example, polynucleotide sequences encoding the polypeptides. It is understood that a polypeptide may contain more than one of the above-described modifications within the same polypeptide.

While peptides may be effective in eliciting a biological activity in vitro, their effectiveness in vivo might be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al., *Pharm. Res.* 10:1268-1273 (1993)). In light of this, it is often advantageous to use modified versions of peptides. The modified peptides retain the structural characteristics of the original L-amino acid peptides that confer the desired biological activity of Ang-(1-7) but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable peptides. Thus, a peptide derivative or peptidomimetic of the present invention may be all L, all D or mixed D, L peptide, in either forward or reverse order. The presence of an N-terminal or C-terminal D-amino acid increases the in vivo stability of a peptide since peptidases cannot utilize a D-amino acid as a substrate (Powell et al., *Pharm. Res.* 10:1268-1273 (1993)). Reverse-D peptides are peptides containing D-amino acids, arranged in a reverse sequence relative to a peptide containing L-amino acids. Thus, the C-terminal residue of an L-amino acid peptide becomes N-terminal for the D-amino acid peptide, and so forth. Reverse D-peptides retain the same secondary conformation and therefore similar activity, as the L-amino acid peptides, but are more resistant to enzymatic degradation in vitro and in vivo, and thus can have greater therapeutic efficacy than the original peptide (Brady and Dodson, *Nature* 368:692-693 (1994); Jameson et al., *Nature* 368:744-746 (1994)). Similarly, a reverse-L peptide may be generated using standard methods where the C-terminus of the parent peptide becomes takes the place of the N-terminus of the reverse-L peptide. It is contemplated that reverse L-peptides of L-amino acid peptides that do not have significant secondary structure (e.g., short peptides) retain the same spacing and conformation of the side chains of the L-amino acid peptide and therefore often have the similar activity as the original L-amino acid peptide. Moreover, a reverse peptide may contain a combination of L- and D-amino acids. The spacing between amino acids and the conformation of the side chains may be retained resulting in similar activity as the original L-amino acid peptide.

Another effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini. Certain chemical modifications, in particular N-terminal glycosylation, have been shown to increase the stability of peptides in human serum (Powell et al., *Pharm. Res.* 10:1268-1273 (1993)). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified peptides consisting of peptides bearing an N-terminal acetyl group and/or a C-terminal amide group.

Substitution of non-naturally-occurring amino acids for natural amino acids in a subsequence of the peptides can also confer resistance to proteolysis. Such a substitution can, for instance, confer resistance to proteolysis by exopeptidases acting on the N-terminus without affecting biological activity. Examples of non-naturally-occurring amino acids include α,α-disubstituted amino acids, N-alkyl amino acids, C-α-methyl amino acids, β-amino acids, and β-methyl amino acids. Amino acids analogs useful in the present invention may include, but are not limited to, β-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine and other unconventional amino acids. Furthermore, the synthesis of peptides with non-naturally-occurring amino acids is routine in the art.

In addition, constrained peptides comprising a consensus sequence or a substantially identical consensus sequence variation may be generated by methods well known in the art (Rizo and Gierasch, *Ann. Rev. Biochem.* 61:387-418 (1992)). For example, constrained peptides may be generated by adding cysteine residues capable of forming disulfide bridges and, thereby, resulting in a cyclic peptide. Cyclic peptides can be constructed to have no free N- or C-termini. Accordingly, they are not susceptible to proteolysis by exopeptidases, although they may be susceptible to endopeptidases, which do not cleave at peptide termini. The amino acid sequences of the peptides with N-terminal or C-terminal D-amino acids and of the cyclic peptides are usually identical to the sequences of the peptides to which they correspond, except for the presence of N-terminal or C-terminal D-amino acid residue, or their circular structure, respectively.

Cyclic Peptides

In some embodiments, a functional equivalent, analogue or derivative of naturally-occurring Ang-(1-7) is a cyclic peptide. As used herein, a cyclic peptide has an intramolecular covalent bond between two non-adjacent residues. The intramolecular bond may be a backbone to backbone, side-chain to backbone or side-chain to side-chain bond (i.e., terminal functional groups of a linear peptide and/or side-chain functional groups of a terminal or interior residue may be linked to achieve cyclization). Typical intramolecular bonds include disulfide, amide and thioether bonds. A variety of means for cyclizing polypeptides are well known in the art, as are many other modifications that can be made to such peptides. For a general discussion, see International Patent Publication Nos. WO 01/53331 and WO 98/02452, the contents of which are incorporated herein by reference. Such cyclic bonds and other modifications can also be applied to the cyclic peptides and derivative compounds of this invention.

Cyclic peptides as described herein may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. Cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Suitable derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Within further embodiments, cyclization may be achieved by amide bond formation. For example, a peptide bond may be formed between terminal functional groups (i.e., the amino and carboxy termini of a linear peptide prior to cyclization). Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate. Methods for forming amide bonds are generally well known in the art. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. Alternatively, cyclization can be performed using the azide method, in which a reactive azide intermediate is generated from an alkyl ester via a hydrazide. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF.

Exemplary Angiotensin-(1-7) Peptides

Linear Angiotensin(1-7) Peptides

In certain aspects, the invention provides linear angiotensin-(1-7) peptides. As discussed above, the structure of naturally-occurring Ang-(1-7) is as follows:

$Asp^1\text{-}Arg^2\text{-}Val^3\text{-}Tyr^o\text{-}Ile^5\text{-}His^6\text{-}Pro^7$ (SEQ ID NO:1)

The peptides and peptide analogs of the invention can be generally represented by the following sequence:

$Xaa^1\text{-}Xaa^2\text{-}Xaa^3\text{-}Xaa^4\text{-}Xaa^5\text{-}Xaa^6\text{-}Xaa^7$ (SEQ ID NO:5), or a pharmaceutically acceptable salt thereof.

$Xaa^1$ is any amino acid or a dicarboxylic acid. In certain embodiments, $Xaa^1$ is Asp, Glu, Asn, Acpc (1-aminocyclopentane carboxylic acid), Ala, Me$_2$Gly (N,N-dimethylglycine), Pro, Bet (betaine, 1-carboxy-N,N,N-trimethylmethanaminium hydroxide), Glu, Gly, Asp, Sar (sarcosine) or Suc (succinic acid). In certain such embodiments, $Xaa^1$ is a negatively-charged amino acid, such as Asp or Glu, typically Asp.

$Xaa^2$ is Arg, Lys, Ala, Cit (citrulline), Orn (ornithine), acetylated Ser, Sar, D-Arg and D-Lys. In certain embodiments, $Xaa^2$ is a positively-charged amino acid such as Arg or Lys, typically Arg.

$Xaa^3$ is Val, Ala, Leu, Nle (norleucine), Ile, Gly, Lys, Pro, HydroxyPro (hydroxyproline), Aib (2-aminoisobutyric acid), Acpc or Tyr. In certain embodiments, $Xaa^3$ is an aliphatic amino acid such as Val, Leu, Ile or Nle, typically Val or Nle.

$Xaa^4$ is Tyr, Tyr(PO$_3$), Thr, Ser, homoSer (homoserine), azaTyr (aza-α'-homo-L-tyrosine) or Ala. In certain embodiments, $Xaa^4$ is a hydroxyl-substituted amino acid such as Tyr, Ser or Thr, typically Tyr.

$Xaa^5$ is Ile, Ala, Leu, norLeu, Val or Gly. In certain embodiments, $Xaa^5$ is an aliphatic amino acid such as Val, Leu, Ile or Nle, typically Ile.

$Xaa^6$ is His, Arg or 6-NH$_2$-Phe (6-aminophenylalanine) In certain embodiments, $Xaa^6$ is a fully or partially positively-charged amino acid such as Arg or His.

$Xaa^7$ is Cys, Pro or Ala.

In certain embodiments, one or more of $Xaa^1\text{-}Xaa^7$ is identical to the corresponding amino acid in naturally-occurring Ang-(1-7). In certain such embodiments, all but one or two of $Xaa^1\text{-}Xaa^7$ are identical to the corresponding amino acid in naturally-occurring Ang-(1-7). In other embodiments, all of $Xaa^1\text{-}Xaa^6$ are identical to the corresponding amino acid in naturally-occurring Ang-(1-7).

In certain embodiments, $Xaa^3$ is Nle. When $Xaa^3$ is Nle, one or more of $Xaa^1\text{-}Xaa^2$ and $Xaa^{4-7}$ are optionally identical to the corresponding amino acid in naturally-occurring Ang-(1-7). In certain such embodiments, all but one or two of $Xaa^1\text{-}Xaa^2$ and $Xaa^{4-7}$ are identical to the corresponding amino acid in naturally-occurring Ang-(1-7). In other embodiments, all of $Xaa^1\text{-}Xaa^2$ and $Xaa^{4-7}$ are identical to the corresponding amino acid in naturally-occurring Ang-(1-7), resulting in the amino acid sequence: Asp 1-$Arg^2$-$Nle^3$-$Tyr^4$-$Ile^5$-$His^6$-$Pro^7$ (SEQ ID NO:2).

In certain embodiments, the peptide has the amino acid sequence $Asp^1\text{-}Arg^2\text{-}Val^3\text{-}Ser^4\text{-}Ile^5\text{-}His^6\text{-}Cys^7$ (SEQ ID NO:6) or $Asp^1\text{-}Arg^2\text{-}Val^3\text{-}ser^4\text{-}Ile^5\text{-}His^6\text{-}Cys7$ (SEQ ID NO:3).

Exemplary Cyclic Angiotensin (1-7) Peptides

In certain aspects, the invention provides a cyclic angiotensin-(1-7) (Ang-(1-7)) peptide analog comprising a linkage, such as between the side chains of amino acids corresponding to positions $Tyr^4$ and $Pro^7$ in Ang. These peptide analogs typically comprise 7 amino acid residues, but can also include a cleavable sequence. As discussed in greater detail below, the invention includes fragments and analogs where one or more amino acids are substituted by another amino acid (including fragments), for example, $Asp^1\text{-}Arg^2\text{-}Val^3\text{-}Ser^4\text{-}Ile^5\text{-}His^6\text{-}Cys^7$ (SEQ ID NO:22), wherein a linkage is formed between $Ser^4$ and $Cys^7$.

Although the following section describes aspects of the invention in terms of a thioether bond linking residues at the 4- and 7-positions, it should be understood that other linkages (as described above) could replace the thioether bridge and that other residues could be cyclized. A thioether bridge is also referred to as a monosulfide bridge or, in the case of Ala-S-Ala, as a lanthionine bridge. Thioether bridge-containing peptides can be formed by two amino acids having one of the following formulas:

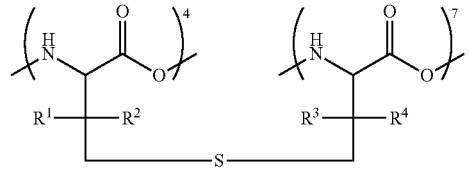

Formula (I)

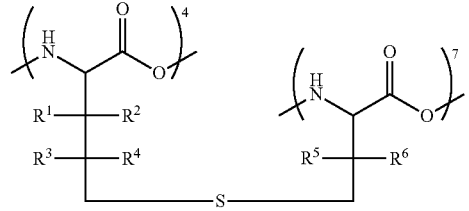

Formula (II)

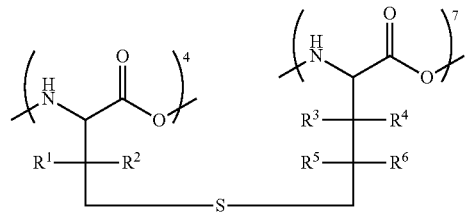

Formula (III)

In these formulae, $R^1$, $R^2$, $R^3$, $R^4$, $R^5$ and $R^6$ are independently —H, an alkyl (e.g., $C_1$-$C_6$ alkyl, $C_1$-$C_4$ alkyl) or an aralkyl group, where the alkyl and aralkyl groups are optionally substituted with one or more halogen, —OH or —NRR' groups (where R and R' are independently —H or $C_1$-$C_4$ alkyl). In certain embodiments, $R^1$, $R^2$, $R^3$, $R^4$, $R^5$ and $R^6$ are each independently —H or —$CH_3$, such where all are —H.

In certain embodiments, the invention provides an Ang analog or derivative comprising a thioether bridge according to formula (I). Typically, $R^1$, $R^2$, $R^3$ and $R^4$ are independently selected from —H and —$CH_3$. Peptides comprising a thioether bridge according to formula (I) can be produced, for example, by lantibiotic enzymes or by sulfur extrusion of a disulfide. In one example, the disulfide from which the sulfur is extruded can be formed by D-cysteine in position 4 and L-cysteine in position 7 or by D-cysteine in position 4 and L-penicillamine in position 7 (see, e.g., Galande, Trent and Spatola (2003) *Biopolymers* 71, 534-551).

In other embodiments, the linkage of the two amino acids can be the bridges depicted in Formula (II) or Formula (III). Peptides comprising a thioether bridge according to Formula (II) can be made, for example, by sulfur extrusion of a disulfide formed by D-homocysteine in position 4 and L-cysteine in position 7. Similarly, peptides comprising a thioether bridge as in Formula (III) can be made, for example, by sulfur extrusion of a disulfide formed by D-cysteine in position 4 and L-homocysteine in position 7.

As discussed above, the Ang analogs and derivatives of the invention vary in length and amino acid composition. The Ang analogs and derivatives of the invention preferably have biological activity or are an inactive precursor molecule that can be proteolytically activated (such as how angiotensin(I), with 10 amino acids, is converted to active fragments by cleavage of 2 amino acids). The size of an Ang analog or derivative can vary but is typically between from about 5 to 10 amino acids, as long as the "core" pentameric segment comprising the 3-7 Nle-thioether-ring structure is encompassed. The amino acid sequence of an analog or derivative of the invention can vary, typically provided that it is biologically active or can become proteolytically activated. Biological activity of an analog or derivative can be determined using methods known in the art, including radioligand binding studies, in vitro cell activation assays and in vivo experiments. See, for example, Godeny and Sayeski, (2006) *Am. J. Physiol. Cell. Physiol.* 291:C1297-1307; Sarr et al., *Cardiovasc. Res.* (2006) 71:794-802; and Koziarz et al., (1933) *Gen. Pharmacol.* 24:705-713.

Ang analogs and derivatives where only the length of the peptide is varied include the following:

a 4,7-cyclized analog designated [$Cyc^{4-7}$]Ang-(1-7), which is derived from natural Ang-(1-7) ($Asp^1$-$Arg^2$-$Val^3$-$Cyc^4$-$Ile^5$-$His^6$-$Cyc^7$, SEQ ID NO:7).

a 4,7-cyclized analog designated [$Nle^3$, $Cyc^{4-7}$]Ang-(1-10), which is derived from natural Angiotensin I (Ang-(1-10)) (Asp 1-$Arg^2$-$Nle^3$-$Cyc^4$-$Ile^5$-$His^6$-$Cyc^7$-$Phe^8$-$His^9$-$Leu^{10}$, SEQ ID NO:8);

a 4,7-cyclized analog designated [$Nle^3$, $Cyc^{4-7}$]Ang-(1-8), which is derived from natural Angiotensin II (Ang-(1-8)) ($Asp^1$-$Arg^2$-$Nle^3$-$Cyc^4$-$Ile^5$-$His^6$-$Cyc^7$-$Phe^8$, SEQ ID NO:9);

a 4,7-cyclised analog designated [$Nle^3$, $Cyc^{4-7}$]Ang-(2-8), which is derived from natural Angiotensin III (Ang-(2-8)) ($Arg^2$-$Nle^3$-$Cyc^4$-$Ile^5$-$His^6$-$Cyc^7$-$Phe^8$, SEQ ID NO:10);

a 4,7-cyclised analog designated [$Nle^3$, $Cyc^{4-7}$]Ang-(3-8), which is derived from natural Angiotensin IV (Ang-(3-8)) ($Nle^3$-$Cyc^4$-$Ile^5$-$His^6$-$Cyc^7$-$Phe^8$, SEQ ID NO:11);

a 4,7-cyclised analog designated [$Nle^3$, $Cyc^{4-7}$]Ang-(1-7) derived from natural Ang-(1-7) ($Asp^1$-$Arg^2$-$Nle^3$-$Cyc^4$-$Ile^5$-$His^6$-$Cyc^7$, SEQ ID NO:12); and a 4,7-cyclised analog designated [$Nle^3$, $Cyc^{4-7}$]Ang-(1-9) derived from natural Ang-(1-9) ($Asp^1$-$Arg^2$-$Nle^3$-$Cyc^4$-$Ile^5$-$His^6$-$Cyc^7$-$Phe^8$-$His^9$, SEQ ID NO:13).

These analogs can have one of the thioether bridges shown in Formulae (I)-(III) as the $Cyc^{4-7}$ moiety, for example, where $Cyc^4$ and $Cyc^7$ are represented by Formula (I), such as where $R^1$-$R^4$ are each —H or —$CH_3$, typically —H.

As compared to the amino acid sequence of the natural angiotensin peptide, the amino acids at positions 4 and 7 of the $Cyc^{4-7}$ analog are modified to allow introduction of the thioether-ring structures shown above. In addition to the length of the Ang analogs, the amino acids at positions other than 3, 4 and 7 can be the same or different from the naturally-occurring peptide, typically provided that the analog retains a biological function. One example is $Asp^1$-$Arg^2$-$Val^3$-$Ser^4$-$Ile^5$-$His^6$-$Cys^7$ (SEQ ID NO:22). For analogs of inactive precursors, like [$Cyc^{4-7}$]Ang-(1-10), biological function refers to one or both of an analog's susceptibility to angiotensin-converting enzymes that can cleave it to a biologically active fragment (e.g. Ang-(1-8) or Ang-(1-7)) or the biological activity of the fragment itself. In certain embodiments, an Ang analog or derivative of the invention has no intrinsic function but inhibits the effects of one or more naturally-occurring angiotensin compounds.

In certain embodiments, an Ang analog of the invention is represented by Formula (IV):

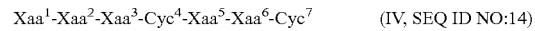

$Xaa^1$-$Xaa^2$-$Xaa^3$-$Cyc^4$-$Xaa^5$-$Xaa^6$-$Cyc^7$ (IV, SEQ ID NO:14)

$Xaa^1$ is any amino acid, but typically a negatively-charged amino acid such as Glu or Asp, more typically Asp.

$Xaa^2$ is a positively-charged amino acid such as Arg or Lys, typically Arg.

$Xaa^3$ is an aliphatic amino acid, such as Leu, Ile or Val, typically Val.

$Cyc^4$ forms a thioether bridge in conjunction with $Cyc^7$. $Cyc^4$ can be a D-stereoisomer and/or a L-stereoisomer, typically a D-stereoisomer. Examples of $Cyc^4$ (taken with $Cyc^7$) are shown in Formulas (I), (II) and (III). Typically, the R groups in Formulae (I), (II) and (III) are —H or —$CH_3$, especially —H.

$Xaa^5$ is an aliphatic amino acid, such as Leu, Ile or Val, typically Ile.

$Xaa^6$ is His.

$Cyc^7$ forms a thioether bridge in conjunction with $Cyc^4$, such as in Formula (I), (II) or (III). $Cyc^7$ can be a D-stereoisomer and/or a L-stereoisomer, typically a L-stereoisomer. Examples of $Cyc^7$ (taken with $Cyc^4$) are shown in Formulas (I), (II) and (III). Typically, the R groups in Formulas (I), (II) and (III) are —H or —$CH_3$, especially —H.

In certain embodiments, one or more of $Xaa^1$-$Xaa^6$ (excluding $Cyc^4$ and $Cyc^7$) is identical to the corresponding amino acid in naturally-occurring Ang-(1-7). In certain such embodiments, all but one or two of $Xaa^1$-$Xaa^6$ are identical to the corresponding amino acid in naturally-occurring Ang-(1-7). In other embodiments, all of $Xaa^1$-$Xaa^6$ are identical to the corresponding amino acid in naturally-occurring Ang-(1-7).

In certain embodiments, $Cyc^4$ and $Cyc^7$ are independently selected from Abu (2-aminobutyric acid) and Ala (alanine), where Ala is present in at least one position. Thus, cyclic analogs can have a thioether linkage formed by -$Ala^4$-S-$Ala^7$- (Formula (I), where $R^1$-$R^4$ are each —H); -$Ala^4$-S-$Abu^7$- (Formula (I): $R^1$-$R^3$ are —H and $R^4$ is —$CH_3$) or -$Abu^4$-S-$Ala^7$- (Formula (I): $R^1$, $R^3$ and $R^4$ are —H and $R^2$ is —$CH_3$). Specific examples of cyclic analogs comprise a -$Abu^4$-S-$Ala^7$- or -$Ala^4$-S-$Ala^7$-linkage.

In certain embodiments, the invention provides an Ang-(1-7) analog with a thioether-bridge between position 4 and position 7 having the amino acid sequence Asp¹-Arg²-Val³-Abu⁴-Ile⁵-His⁶-Ala⁷ (SEQ ID NO:15) or the amino acid sequence Asp¹-Arg²-Val³-Ala⁴-Ile⁵-His⁶-Ala⁷ (SEQ ID NO:16), which are represented by the following structural diagrams:

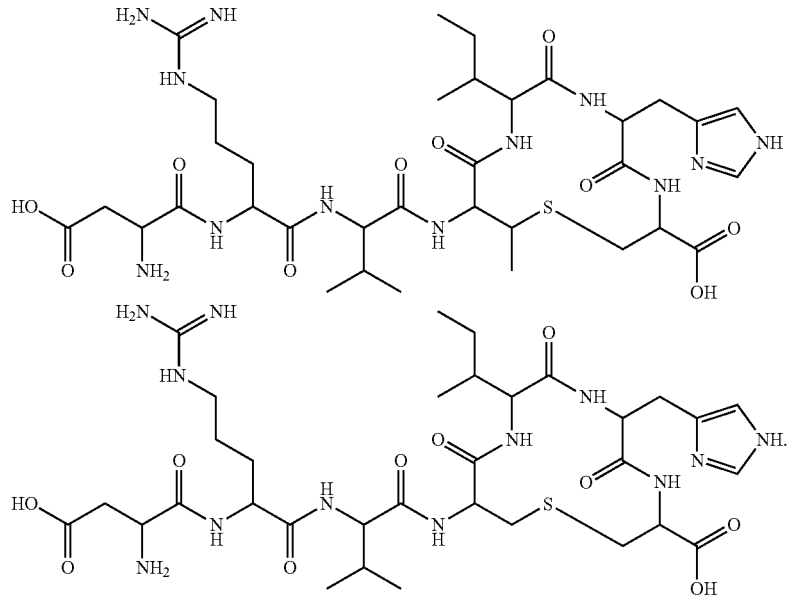

In certain embodiments, an Ang analog or derivative of the invention is represented by Formula (V):

Xaa¹-Xaa²-Nle³-Cyc⁴-Xaa⁵-Xaa⁶-Cyc⁷-Xaa⁸-Xaa⁹-Xaa¹⁰ (V, SEQ ID NO:17) As discussed above, one or more of Xaa¹, Xaa², Xaa⁸, Xaa⁹ and Xaa¹⁰ are absent in certain embodiments. For example, (1) Xaa¹⁰ is absent, (2) Xaa⁹ and Xaa¹⁰ are absent, (3) Xaa⁸, Xaa⁹ and Xaa¹⁰ are absent, (4) Xaa¹ is absent, (5) Xaa¹ and Xaa¹⁰ are absent, (6) Xaa¹, Xaa⁹ and Xaa¹⁰ are absent, (7) Xaa¹, Xaa⁸, Xaa⁹ and Xaa¹⁰ are absent, (8) Xaa¹ and Xaa² are absent, (9) Xaa¹, Xaa² and Xaa¹⁰ are absent, (10) Xaa¹, Xaa², Xaa⁹ and Xaa¹⁰ are absent, or (11) Xaa¹, Xaa², Xaa⁸, Xaa⁹ and Xaa¹⁰ are absent. For each of these embodiments, the remaining amino acids have the values described below.

Xaa¹, when present, is any amino acid, but typically a negatively charged amino acid such as Glu or Asp, more typically Asp.

Xaa², when present, is a positively charged amino acid such as Arg or Lys, typically Arg.

Nle³ is norleucine.

Cyc⁴ forms a thioether bridge in conjunction with Cyc⁷. Cyc⁴ can be a D-stereoisomer and/or a L-stereoisomer, typically a D-stereoisomer. Examples of Cyc⁴ (taken with Cyc⁷) are shown in Formulas (I), (II) and (III). Typically, the R groups in Formulae (I), (II) and (III) are —H or —CH₃, especially —H.

Xaa⁵ is an aliphatic amino acid, such as Leu, Nle, Ile or Val, typically Ile.

Xaa⁶ is His.

Cyc⁷ forms a thioether bridge in conjunction with Cyc⁴, such as in Formula (I), (II) or (III). Cyc⁷ can be a D-stereoisomer and/or a L-stereoisomer, typically a L-stereoisomer. Examples of Cyc⁷ (taken with Cyc⁴) are shown in Formulas (I), (II) and (III). Typically, the R groups in Formulae (I), (II) and (III) are —H or —CH₃, especially —H.

Xaa⁸, when present, is an amino acid other than Pro, typically Phe or Ile. In certain embodiments, Ile results in an inhibitor of Ang(1-8). In certain embodiments, Phe maintains the biological activity of Ang(1-8) or Ang(1-10).

Xaa⁹, when present, is His.

Xaa¹⁰, when present, is an aliphatic residue, for example, Ile, Val or Leu, typically Leu.

In certain embodiments, one or more of Xaa¹-Xaa¹⁰ (excluding Nle³, Cyc⁴ and Cyc⁷) is identical to the corresponding amino acid in naturally-occurring Ang (including Ang-(1-7), Ang(1-8), Ang(1-9), Ang(1-10), Ang(2-7), Ang(2-8), Ang(2-9), Ang(2-10), Ang(3-8), Ang(3-9) and Ang(3-10). In certain such embodiments, all but one or two of Xaa¹-Xaa¹⁰ (for those present) are identical to the corresponding amino acid in naturally-occurring Ang. In other embodiments, all of Xaa¹-Xaa¹⁰ (for those present) are identical to the corresponding amino acid in naturally-occurring Ang.

In certain embodiments, Cyc⁴ and Cyc⁷ are independently selected from Abu (2-aminobutyric acid) and Ala (alanine), where Ala is present at at least one position. Thus, encompassed are cyclic analogs comprising a thioether linkage formed by -Ala⁴-S-Ala⁷- (Formula (I), where R¹-R⁴ are each —H); -Ala⁴-S-Abu⁷- (Formula (I): R¹-R³ are —H and R⁴ is —CH₃) or -Abu⁴-S-Ala⁷- (Formula (I): R¹, R³ and R⁴ are —H and R² is —CH₃). Specific cyclic analogs comprise a -Abu⁴-S-Ala⁷- or -Ala⁴-S-Ala⁷-linkage.

In particular, the invention provides an Ang-(1-7) analog or derivative with a thioether-bridge between position 4 and position 7 having the amino acid sequence Asp¹-Arg²-Nle³-Abu⁴-Ile⁵-His⁶-Ala⁷ (SEQ ID NO:18) or the amino acid sequence Asp¹-Arg²-Nle³-Ala⁴-Ile⁵-His⁶-Ala⁷ (SEQ ID NO:19).

In another aspect, the invention provides an Ang-(1-8) analog or derivative with a thioether-bridge between position 4 and position 7 having Ang-(1-8) antagonistic activity, in particular an Ang(1-8) analog or derivative having the amino acid sequence Asp¹-Arg²-Nle³-Abu⁴-Ile⁵-His⁶-Ala⁷-Ile⁸ (SEQ ID NO:20) or the amino acid sequence Asp¹-Arg²-Nle³-Ala⁴-Ile⁵-His⁶-Ala⁷-Ile⁸ (SEQ ID NO:21).

Ang (1-7) Receptor Agonists

In some embodiments, the present invention provides methods of treating diabetes including administering to a subject who is suffering from or susceptible to diabetes an angiotensin (1-7) receptor agonist. As used herein, the term "angiotensin-(1-7) receptor agonist" encompasses any molecule that has a positive impact in a function of an angiotensin-(1-7) receptor, in particular, the G-protein coupled Mas receptor. In some embodiments, an angiotensin-(1-7) receptor agonist directly or indirectly enhances, strengthens, activates and/or increases an angiotensin-(1-7) receptor (i.e., the Mas receptor) activity. In some embodiments, an angiotensin-(1-7) receptor agonist directly interacts with an angiotensin-(1-7) receptor (i.e., the Mas receptor). Such agonists can be peptidic or non-peptidic including, e.g., proteins, chemical compounds, small molecules, nucleic acids, antibodies, drugs, ligands, or other agents. In some embodiments, the angiotensin (1-7) receptor agonist is a non-peptidic agonist.

An exemplary class of angiotensin-(1-7) receptor agonists are 1-(p-thienylbenzyl)imidazoles. Examples of these non-peptide angiotensin-(1-7) receptor agonists are represented by Structural Formula (VI):

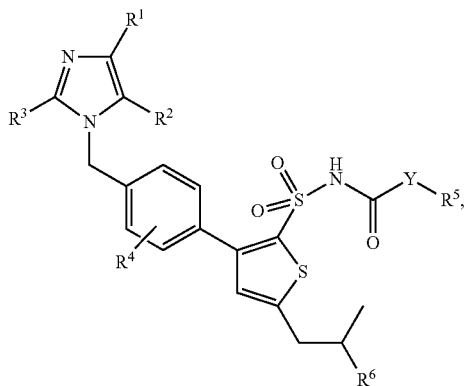

(VI)

or pharmaceutically acceptable salts thereof, wherein:

$R^1$ is halogen, hydroxyl, $(C_1-C_4)$-alkoxy, $(C_1-C_8)$-alkoxy wherein 1 to 6 carbon atoms are replaced by the heteroatoms O, S, or NH (preferably by O), $(C_1-C_4)$-alkoxy substituted by a saturated cyclic ether such as tetrahydropyran or tetrahydrofuran, O—$(C_1-C_4)$-alkenyl, O—$(C_1-C_4)$-alkylaryl, or aryloxy that is unsubstituted or substituted by a substituent selected from halogen, $(C_1-C_3)$-alkyl, $(C_1-C_3)$-alkoxy and trifluoromethyl;

$R^2$ is CHO, COOH, or (3) CO—O—$(C_1-C_4)$-alkyl;

$R^3$ is $(C_1-C_4)$-alkyl or aryl;

$R^4$ is hydrogen, halogen (chloro, bromo, fluoro), or $(C_1-C_4)$-alkyl;

X is oxygen or sulfur;

Y is oxygen or —NH—;

$R^5$ is hydrogen, $(C_1-C_6)$-alkyl; or $(C_1-C_4)$-alkylaryl, where $R^5$ is hydrogen when Y is —NH—; and $R^6$ is $(C_1-C_5)$-alkyl.

In certain embodiments, $R^1$ is not halogen when $R^2$ is COOH or CO—O—$(C_1-C_4)$-alkyl.

In some embodiments, an angiotensin-(1-7) receptor agonist is AVE 0991, 5-formyl-4-methoxy-2-phenyl-[[4-[2-(ethylamino carbonylsulfonamido)-5-isobutyl-3-thienyl]-phenyl]-methyl]-imidazole, which is represented by the following structure:

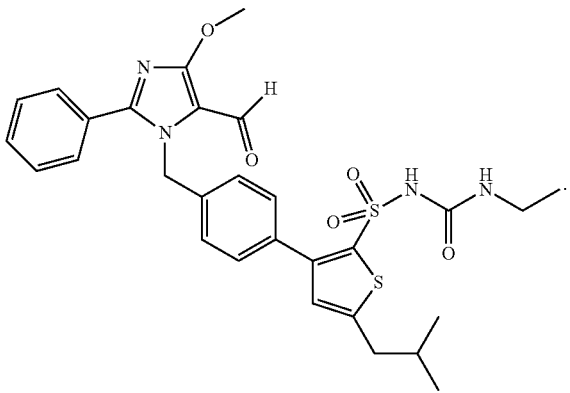 [SMILES: CCNC(=O)NS(=O)(=O)c1sc(CC(C)C)cc1-c1ccc(Cn2c(-c3ccccc3)nc(OC)c2C=O)cc1]

Another exemplary class of angiotensin-(1-7) receptor agonists are p-thienylbenzylamides. Examples of these non-peptide angiotensin-(1-7) receptor agonists are represented by Structural Formula (VII):

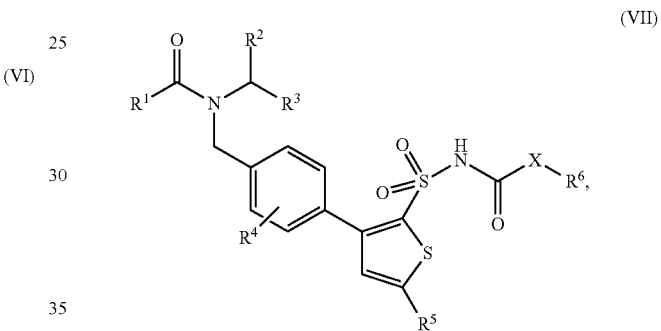

(VII)

or a pharmaceutically acceptable salt thereof, wherein:

$R^1$ is $(C_1-C_5)$-alkyl that is unsubstituted or substituted by a radical chosen from $NH_2$, halogen, O—$(C_1-C_3)$-alkyl, CO—O—$(C_1-C_3)$-alkyl and $CO_2H$, $(C_3-C_8)$-cycloalkyl, $(C_1-C_3)$-alkyl-$(C_3-C_8)$-cycloalkyl, $(C_6-C_{10})$-aryl that is unsubstituted or substituted by a radical chosen from halogen and O—$(C_1-C_3)$-alkyl, $(C_1-C_3)$-alkyl-$(C_6-C_{10})$-aryl where the aryl radical is unsubstituted or substituted by a radical chosen from halogen and O—$(C_1-C_3)$-alkyl, $(C_1-C_5)$-heteroaryl, or $(C_1-C_3)$-alkyl-$(C_1-C_5)$-heteroaryl;

$R^2$ is hydrogen, $(C_1-C_6)$-alkyl that is unsubstituted or substituted by a radical chosen from halogen and O—$(C_1-C_3)$-alkyl, $(C_3-C_8)$-cyclo alkyl, $(C_1-C_3)$-alkyl-$(C_3-C_8)$-cycloalkyl, $(C_6-C_{10})$-aryl that is unsubstituted or substituted by a radical chosen from among halogen, O—$(C_1-C_3)$-alkyl and CO—O—$(C_1-C_3)$-alkyl, or $(C_1-C_3)$-alkyl-$(C_6-C_{10})$-aryl that is unsubstituted or substituted by a radical chosen from halogen and O—$(C_1-C_3)$-alkyl;

$R^3$ is hydrogen, COOH, or COO—$(C_1-C_4)$-alkyl;

$R^4$ is hydrogen, halogen; or $(C_1-C_4)$-alkyl;

$R^5$ is hydrogen or $(C_1-C_6)$-alkyl;

$R^6$ is hydrogen, $(C_1-C_6)$-alkyl, $(C_1-C_3)$-alkyl-$(C_3-C_8)$-cycloalkyl, or $(C_2-C_6)$-alkenyl; and X is oxygen or NH.

Additional examples of angiotensin-(1-7) receptor agonists are described in U.S. Pat. No. 6,235,766, the contents of which are incorporated by reference herein.

Various angiotensin-(1-7) receptor agonists described above can be present as pharmaceutically acceptable salts. As used herein, "a pharmaceutically acceptable salt" refers to salts that retain the desired activity of the peptide or equivalent compound, but preferably do not detrimentally affect the activity of the peptide or other component of a system, which uses the peptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts formed from a cationic material may utilize the conjugate base of these inorganic and organic acids. Salts may also be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g., a zinc tannate salt). The non-toxic, physiologically acceptable salts are preferred.

The salts can be formed by conventional means such as by reacting the free acid or free base forms of the product with one or more equivalents of the appropriate acid or base in a solvent or medium in which the salt is insoluble, or in a solvent such as water which is then removed in vacuo or by freeze-drying, or by exchanging the cations of an existing salt for another cation on a suitable ion exchange resin.

An alkyl group is a straight chained or branched non-aromatic hydrocarbon that is completely saturated. Typically, a straight chained or branched alkyl group has from 1 to about 20 carbon atoms, preferably from 1 to about 10. Examples of straight chained and branched alkyl groups include methyl, ethyl, n-propyl, iso-propyl, n-butyl, sec-butyl, tert-butyl, pentyl, hexyl, pentyl and octyl. A C1-C4 straight chained or branched alkyl group is also referred to as a "lower alkyl" group.

An alkenyl group is a straight chained or branched non-aromatic hydrocarbon that is includes one or more double bonds. Typically, a straight chained or branched alkenyl group has from 2 to about 20 carbon atoms, preferably from 2 to about 10. Examples of straight chained and branched alkenyl groups include ethenyl, n-propenyl, and n-butenyl.

Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl. Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

An aralkyl group is an alkyl group substituted by an aryl group. Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrrolyl, pyrazinyl, thiazolyl, oxazolyl, and tetrazolyl. Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

Pharmaceutical Compositions

In accordance with the methods of the invention, an Ang peptide or angiotensin (1-7) receptor agonist of the invention as described herein can be administered to a subject alone (e.g., as a purified peptide or compound), or as a component of a composition or medicament (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration. Methods of formulating compositions are known in the art (see, e.g., Remington's Pharmaceuticals Sciences, 17$^{th}$ Edition, Mack Publishing Co., (Alfonso R. Gennaro, editor) (1989)).

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulations can include standard carriers such as pharmaceutical grades of mannitol, lactose, starch, magnesium stearate, polyvinyl pyrrolidone, sodium saccharine, cellulose, magnesium carbonate, etc.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In some embodiments, provided compositions, including those provided as pharmaceutical formulations, comprise a liquid carrier such as but not limited to water, saline, phosphate buffered saline, Ringer's solution, dextrose solution, serum-containing solutions, Hank's solution, other aqueous physiologically balanced solutions, oils, esters and glycols.

An Ang peptide or angiotensin (1-7) receptor agonist as described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

An Ang peptide or angiotensin (1-7) receptor agonist as described herein (or a composition or medicament containing an Ang peptide or Angiotensin (1-7) receptor agonist as described herein) may be administered by any appropriate route. In some embodiments, an Ang peptide or Angiotensin (1-7) receptor agonist as described herein is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, an Ang peptide or Angiotensin (1-7) receptor agonist as described herein is administered intravenously. In some embodiments, an Ang peptide or Angiotensin (1-7) receptor agonist as described herein is administered orally. In other embodiments, an Ang peptide or Angiotensin (1-7) receptor agonist as described herein is administered by direct administration to a target tissue, such as heart or muscle (e.g., intramuscular), tumor (intratumorally), nervous system (e.g., direct injection into the brain; intraventricularly; intrathecally). Alternatively, an Ang peptide or Angiotensin (1-7) receptor agonist as described herein (or a composition or medicament containing an Ang peptide described herein) can be administered by inhalation, parenterally, intradermally, transdermally, or transmucosally (e.g., orally or nasally). More than one route can be used concurrently, if desired.

Dosing

In some embodiments, a composition is administered in a therapeutically effective amount and/or according to a dosing regimen that is correlated with a particular desired outcome (e.g., with treating or reducing risk for Diabetes).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce blood glucose levels by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. For example, in some embodiments, an appropriate dose or amount is a dose or amount sufficient to reduce incidence of Diabetes by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100%. Alternatively or additionally, in some embodiments, an appropriate dose or amount is determined through use of one or more in vitro or in vivo assays to help identify desirable or optimal dosage ranges or amounts to be administered.

In various embodiments, an Ang peptide or Angiotensin (1-7) receptor agonist is administered at a therapeutically effective amount. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

Therapeutically effective dosage amounts of angiotensin (1-7) peptides or angiotensin (1-7) receptor agonists, including derivatives, analogs, and/or salts may be present in varying amounts in various embodiments. In some embodiments, a therapeutically effective dosage amount can be, for example, about 1-10,000 µg/kg, about 5-1,500 µg/kg, about 100-1,000 µg/kg, or 50-500 µg/kg. In some embodiments, the therapeutically effective dosage amount can be, for example, about 1 µg/kg, 2.5 µg/kg, 5 µg/kg, 10 µg/kg, 20 µg/kg, 30 µg/kg, 40 µg/kg, 50 µg/kg, 60 µg/kg, 70 µg/kg, 80 µg/kg, 90 µg/kg, 100 µg/kg, 150 µg/kg, 200 µg/kg, 250 µg/kg, 300 µg/kg, 400 µg/kg, 500 µg/kg, 600 µg/kg, 700 µg/kg, 800 µg/kg, 900 µg/kg, 1000 µg/kg, or 1500 µg/kg. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.001 mg/kg weight to about 1 mg/kg weight, e.g. from about 0.001 mg/kg weight to about 0.9 mg/kg weight, from about 0.001 mg/kg weight to about 0.8 mg/kg weight, from about 0.001 mg/kg weight to about 0.8 mg/kg weight, from about 0.001 mg/kg weight to about 0.7 mg/kg weight, from about 0.001 mg/kg weight to about 0.6 mg/kg weight, from about 0.001 mg/kg weight to about 0.5 mg/kg weight, from about 0.01 mg/kg weight to about 1 mg/kg weight, from about 0.01 mg/kg weight to about 0.9 mg/kg weight, from about 0.01 mg/kg weight to about 0.8 mg/kg weight, from about 0.01 mg/kg weight to about 0.7 mg/kg weight, from about 0.01 mg/kg weight to about 0.6 mg/kg weight, from about 0.01 mg/kg weight to about 0.5 mg/kg weight, from about 0.02 mg/kg weight to about 1 mg/kg weight, from about 0.02 mg/kg weight to about 0.9 mg/kg weight, from about 0.02 mg/kg weight to about 0.8 mg/kg weight, from about 0.02 mg/kg weight to about 0.7 mg/kg weight, from about 0.02 mg/kg weight to about 0.6 mg/kg weight, from about 0.02 mg/kg weight to about 0.5 mg/kg weight, from about 0.03 mg/kg weight to about 1 mg/kg weight, from about 0.03 mg/kg weight to about 0.9 mg/kg weight, from about 0.03 mg/kg weight to about 0.8 mg/kg weight, from about 0.03 mg/kg weight to about 0.7 mg/kg weight, from about 0.03 mg/kg weight to about 0.6 mg/kg weight, from about 0.03 mg/kg weight to about 0.5 mg/kg weight, from about 0.04 mg/kg weight to about 1 mg/kg weight, from about 0.04 mg/kg weight to about 0.9 mg/kg weight, from about 0.04 mg/kg weight to about 0.8 mg/kg weight, from about 0.04 mg/kg weight to about 0.7 mg/kg weight, from about 0.04 mg/kg weight to about 0.6 mg/kg weight, from about 0.04 mg/kg weight to about 0.5 mg/kg weight, from about 0.05 mg/kg weight to about 1 mg/kg weight, from about 0.05 mg/kg weight to about 0.9 mg/kg weight, from about 0.05 mg/kg weight to about 0.8 mg/kg weight, from about 0.05 mg/kg weight to about 0.7 mg/kg weight, from about 0.05 mg/kg weight to about 0.6 mg/kg weight, from about 0.05 mg/kg weight to about 0.5 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In some embodiments, the angiotensin (1-7) peptide is administered at an effective dose ranging from about 1-1,000 µg/kg/day (e.g., ranging from about 1-900 µg/kg/day, 1-800 µg/kg/day, 1-700 µg/kg/day, 1-600 µg/kg/day, 1-500 µg/kg/day, 1-400 µg/kg/day, 1-300 µg/kg/day, 1-200 µg/kg/day, 1-100 µg/kg/day, 1-90 µg/kg/day, 1-80 µg/kg/day, 1-70 µg/kg/day, 1-60 µg/kg/day, 1-50 µg/kg/day, 1-40 µg/kg/day, 1-30 µg/kg/day, 1-20 µg/kg/day, 1-10 µg/kg/day). In some embodiments, the angiotensin (1-7) peptide is administered at an effective dose ranging from about 1-500 µg/kg/day. In some embodiments, the angiotensin (1-7) peptide is administered at an effective dose ranging from about 50-500 µg/kg/day. In some embodiments, the angiotensin (1-7) peptide is administered at an effective dose ranging from about 1-100 µg/kg/day. In some embodiments, the angiotensin (1-7) peptide is administered at an effective dose ranging from about 1-60 µg/kg/day. In some embodiments, the angiotensin (1-7) peptide is administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 µg/kg/day.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of Diabetes.

In some embodiments, a formulation comprising an Ang peptide or Angiotensin (1-7) receptor agonist as described herein administered as a single dose. In some embodiments, a formulation comprising an Ang peptide or Angiotensin (1-7) receptor agonist as described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising an Ang peptide or Angiotensin (1-7) receptor agonist as described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising an Ang peptide or Angiotensin (1-7) receptor agonist as described herein is administered at regular intervals indefinitely. In some embodiments, a formulation comprising an Ang peptide or Angiotensin (1-7) receptor agonist as described herein is administered at regular intervals for a defined period. In some embodiments, a formulation comprising an Ang peptide or Angiotensin (1-7) receptor agonist as described herein is administered at regular intervals for 5 years, 4, years, 3, years, 2, years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day.

Combination Therapy

In some embodiments, an Ang peptide is administered in combination with one or more known therapeutic agents (e.g., anti-diabetic medications) currently used for Diabetes prophylaxis and treatment. In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

Kits

The present invention further provides kits or other articles of manufacture which contains an Ang peptide or a formulation containing the same and provides instructions for its reconstitution (if lyophilized) and/or use. Kits or other articles of manufacture may include a container, a syringe, vial and any other articles, devices or equipment useful in administration (e.g., subcutaneous, oral, by inhalation). Suitable containers include, for example, bottles, vials, syringes (e.g., pre-filled syringes), ampules, cartridges, reservoirs, or lyo-jects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may hold formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration. In some embodiments, a container may contain a single dose of a stable formulation containing an Ang peptide. In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 20 mg/ml, at least 30 mg/ml, at least 40 mg/ml, at least 50 mg/ml, at least 75 mg/ml, at least 100 mg/ml). Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

The invention will be more fully understood by reference to the following examples. They should not, however, be construed as limiting the scope of the invention. All literature citations are incorporated by reference.

EXEMPLIFICATION

Example 1

Angiotensin-(1-7) and PanCyte Treatment in the Streptozotocin (STZ) Induced Diabetic Mouse Model Streptozotocin is a widely used chemical agent for producing Type-I Diabetes in experimental animals. The chemical is thought to cause Diabetes by direct action on the pancreatic beta cells and inhibits the insulin secretory mechanism. Depending upon the dosing regimen, streptozotocin can cause a mild, moderate, or severe diabetic condition.

C57Bl/6 female, 7-8 weeks old were used for the study. Upon arrival, mice were 6 weeks of age. All the mice were obtained from The Jackson Laboratory, Bar Harbor, Me. 04609, USA.

Conditions conformed to Standard Operating Procedure which is based on the "Guide for the Care and Use of Laboratory Animals". Mice were fed TEKLAD 2018-Global 18% rodent diet, provided ad libitum. Arrowhead Drinking was water provided ad libitum. Mice were maintained in a controlled environment with a temp 70-72° F., humidity 30-70%, with a photo cycle of 12 hours of light and 12 hours of dark.

The mice were acclimatized for a period of at least 7 days. A thorough physical examination was performed before selecting the mice. Only mice free of obvious health abnormalities indicative of health problems were used for the study.

Historically mice are found to be a suitable model for pre-clinical evaluation studies and are recommended by regulatory agencies. STZ induced diabetic mouse model is a standard and commonly used model for evaluation of diabetes drugs. Therefore, this species and strain was a reasonable alternative for evaluating the therapeutic properties of test compounds.

Following acclimatization, mice were dosed intraperitoneally (IP) with 50 mg/kg STZ solubilized in 0.05 M sodium citrate at a volume of 100 µl per mouse for five consecutive days. Blood Glucose levels were monitored beginning day 4 post STZ using a glucose meter (Accu-Chek Advantage from Roche). On day six (after five days of STZ injection) mice were grouped into four groups having average blood glucose levels of 200 mg/dL. Two groups were dosed with PanCyte (SEQ ID NO:22) 50 and 500 µg/kg body weight respectively, one group was dosed with TXA-127 (SEQ ID NO:1) 500 ug/kg, and one group was dosed with PBS as vehicle control.

Blood glucose was be monitored 3×/week for 4 weeks post STZ. Blood glucose levels was be monitored using a glucose meter by placing a drop of blood directly on to the meter strip, and measuring according to manufacturer's instructions. Blood glucose over the course of the experiment is shown in FIG. 1. The data presented herein suggest that administration of both 50 and 500 µg/kg body weight of PanCyte results in decreased blood glucose levels in the STZ induced diabetic mouse model.

Figure 2:
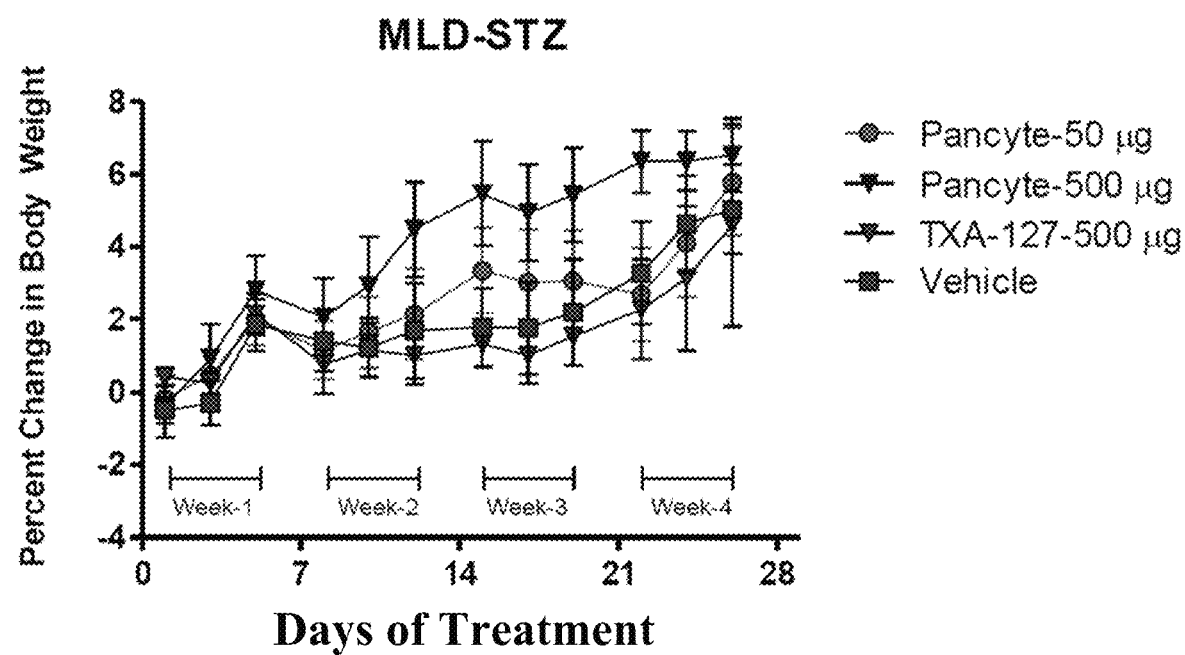
FIG. 2 shows an exemplary graph of percent change in body weight over 28 daysweeks as a function of time in the streptozotocin induced diabetic mouse model in the same animals and treatment conditions shown in FIG. 1.

Body Weight was monitored 3×/week for 4 weeks post STZ. Body weight was monitored using a laboratory balance. Percent body weight change over the course of the experiment is shown in FIG. 2. The data presented herein suggest that administration of both 50 and 500 μg/kg body weight of PanCyte had little effect in the STZ induced diabetic mouse model.

Figure 3:
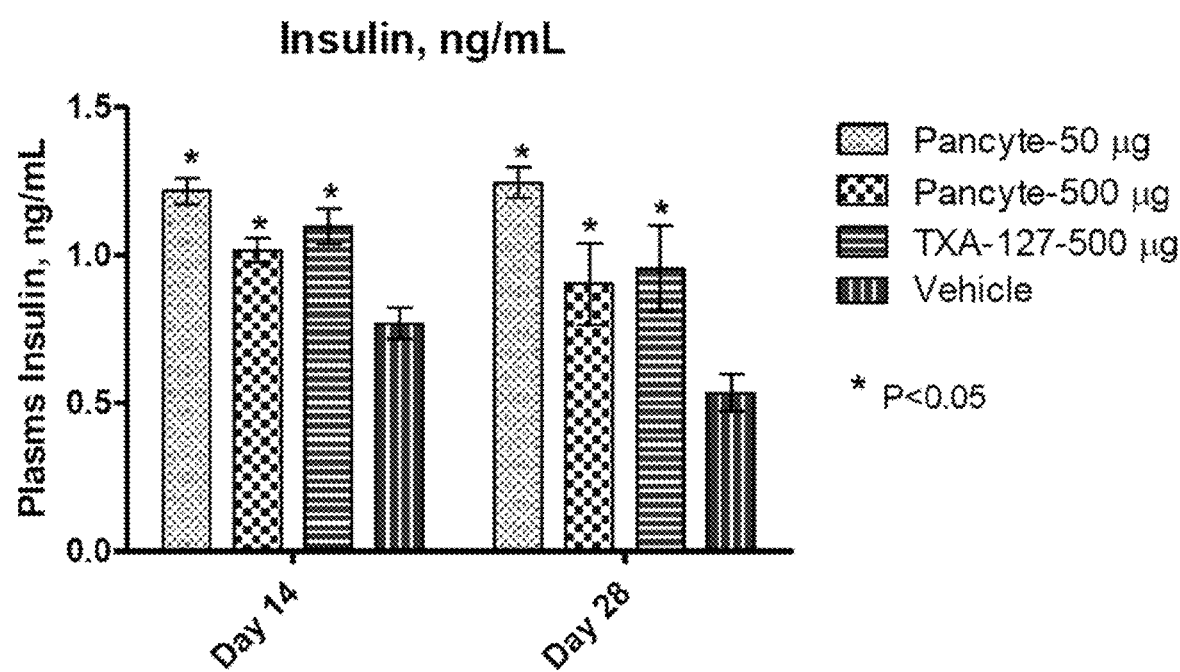
FIG. 3 shows an exemplary graph of plasma insulin levels in ng/mL on days 14 and 28 after treatment in the streptozotocin induced diabetic mouse model in the same animals and treatment conditions shown in FIG. 1.

Plasma insulin levels were measured on days 14 and 28 after treatment. Blood samples (approximately 50 to 100 ul) were collected and processed for plasma by centrifugation. Plasma samples were then used for the measurement of insulin levels using a mouse sensitive insulin ELISA kit (ALPCO Diagnostic), according the to manufacturer's instructions. Plasma insulin levels, in ng/mL, are shown in FIG. 3 and Table 1. The data suggest that treatment with any of 50 ug/kg weight PanCyte, 500 ug/kg weight Pancyte, or 500 ug/kg weight TXA-127 result in significantly higher levels of insulin as compared to vehicle treated control.

TABLE 1

Insulin Levels (ng/ml).

Insulin, ng/ml (Mean ± SEM)

| | Pancyte-50 μg | | | Pancyte-500 μg | | | TXA-127-500 μg | | | Vehicle | | |
|---|---|---|---|---|---|---|---|---|---|---|---|---|
| Day | Mean | SEM | N | Mean | SEM | N | Mean | SEM | N | Mean | SEM | N |
| 14 | 1.217 | 0.045 | 10 | 1.016 | 0.041 | 10 | 1.097 | 0.061 | 10 | 0.770 | 0.053 | 10 |
| 28 | 1.244 | 0.050 | 10 | 0.902 | 0.137 | 10 | 0.954 | 0.145 | 10 | 0.534 | 0.062 | 10 |

At the end of the study mice were euthanized using $CO_2$ asphyxiation and pancreas was removed and flash frozen and stored at −80 degrees C.

Example 2

Treatment with Angiotensin-(1-7), PanCyte, and Linear PanCyte in the Streptozotocin (STZ) Induced Diabetic Mouse Model C57Bl/6 female mice, 6-7 weeks old were used for the study and conditions were the same as for Example 1 above unless otherwise specified. Following acclimatization, mice were dosed intraperitoneally (IP) with 50 mg/kg STZ solubilized in 0.05 M sodium citrate buffer at a volume of 100 μl per mouse for five consecutive days. Blood Glucose levels were monitored on day 6 post STZ using Accu check glucose meter. Mice were grouped having average blood glucose levels of 200 mg/dL. There were three groups of ten mice each. Mice were dosed subcutaneously with Linear PanCyte (SEQ ID NO:6), PanCyte or vehicle for twenty-eight days.

Following acclimatization, mice were dosed intraperitoneally (IP) with 50 mg/kg STZ solubilized in 0.05 M sodium citrate at a volume of 100 μl per mouse for five consecutive days. Blood Glucose levels were monitored beginning day 4 post STZ using Accu check glucose meter. On day six (after five days of STZ injection) mice were grouped in to four groups having average blood glucose levels of 200 mg/dL. Experimental groups were as follows:

TABLE 2

Group Design.

| Group | | Dose Concentration | N | ROA | Dosing Volume | Dosing Frequency |
|---|---|---|---|---|---|---|
| 1 | Vehicle Control (PBS) | PBS | 10 | SC | 100 μl/mouse | Once Daily for 28 Days |
| 2 | Linear PanCyte | 50 μg/kg | 10 | SC | 100 μl/mouse | |
| 3 | PanCyte | 50 μg/kg | 10 | SC | 100 μl/mouse | |

Linear PanCyte and PanCyte were prepared in saline and administrated subcutaneously at a dose volume of 100 μl/mouse daily for twenty-eight days. Dosing solutions were prepared fresh every three days.

Figure 4:
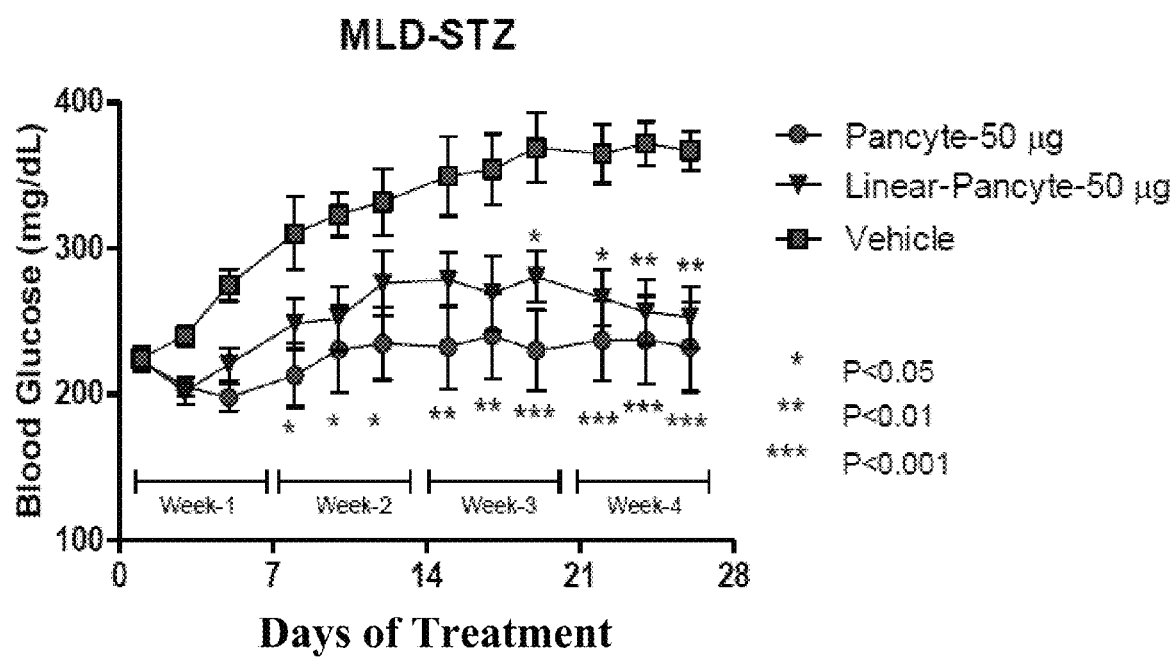
FIG. 4 shows an exemplary graph of blood glucose in mg/dL over 28 days plotted as a function of time in the streptozotocin induced diabetic mouse model. STZ induced diabetic mice were dosed with 50 µg/kg of linear PanCyte (SEQ ID NO:5), 50 µg/kg of cyclized PanCyte, or PBS as vehicle control.

Blood Glucose levels were measured 3×/week for twenty eight days are presented in FIG. 4 and Table 3. Significant differences were observed with the groups treated with PanCyte 50 μg/kg and Linear-PanCyte 50 μg/kg dose as compared to vehicle treated group. No significant differences were observed between the treatment groups. The blood glucose level was lowest in the groups treated with PanCyte 50 μg/kg followed by Linear-PanCyte 50 μg/kg.

TABLE 3

Blood Glucose Levels.

Blood Glucose, mg/dl

| | Pancyte-50 μg | | | Linear-Pancyte-50 μg | | | Vehicle | | |
|---|---|---|---|---|---|---|---|---|---|
| Day | Mean | SEM | N | Mean | SEM | N | Mean | SEM | N |
| 1 | 223 | 7.31 | 10 | 222.8 | 5.01 | 10 | 224.9 | 7.90 | 10 |
| 3 | 205.3 | 6.77 | 10 | 202.2 | 9.25 | 10 | 240 | 7.17 | 10 |
| 5 | 197.8 | 9.26 | 10 | 220.7 | 10.90 | 10 | 274.9 | 11.03 | 10 |
| 8 | 213.2 | 21.80 | 10 | 248.5 | 17.44 | 10 | 310.4 | 25.35 | 10 |
| 10 | 230.7 | 29.62 | 10 | 252.1 | 22.06 | 10 | 323.4 | 15.09 | 10 |
| 12 | 234.8 | 24.74 | 10 | 276.1 | 22.60 | 10 | 331.8 | 22.76 | 10 |
| 15 | 232.5 | 28.73 | 10 | 278.6 | 18.69 | 10 | 349.5 | 27.19 | 10 |
| 17 | 240.3 | 29.37 | 10 | 269.3 | 25.77 | 10 | 354.2 | 24.42 | 10 |
| 19 | 230 | 27.92 | 10 | 280.7 | 17.63 | 10 | 369.2 | 23.65 | 10 |
| 22 | 237.1 | 27.70 | 10 | 266.2 | 19.06 | 10 | 364.8 | 20.29 | 10 |
| 24 | 237.3 | 29.95 | 10 | 256.3 | 21.75 | 10 | 372 | 14.79 | 10 |
| 26 | 232.6 | 30.82 | 10 | 253 | 21.17 | 10 | 367 | 13.55 | 10 |

Figure 5:
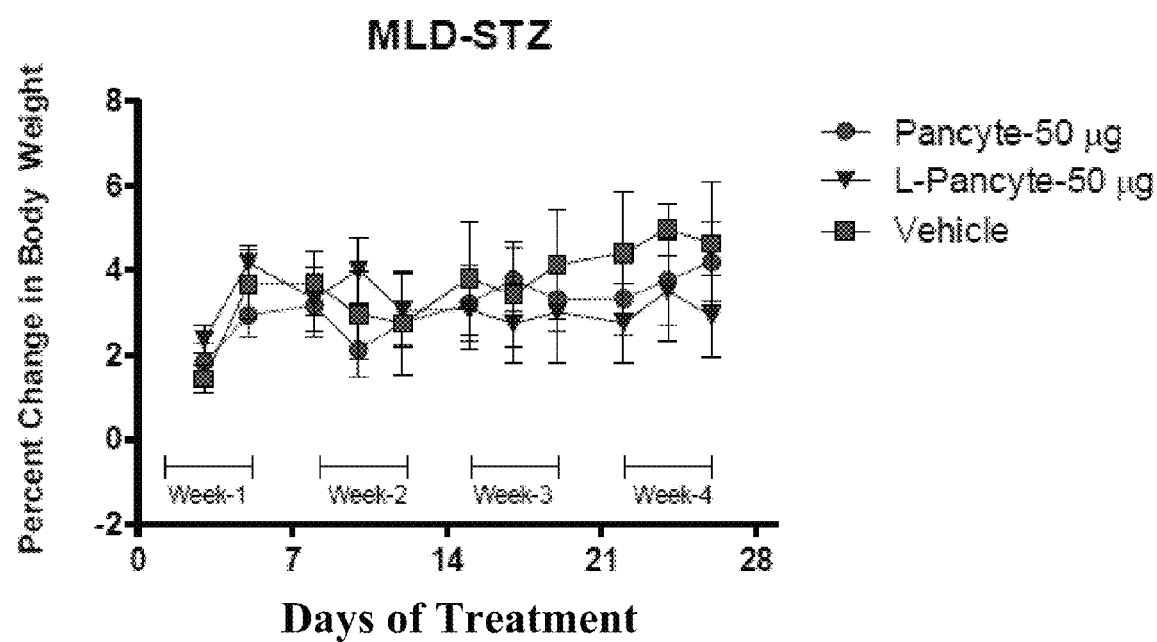
FIG. 5 shows an exemplary graph of percent change in body weight over 28 days as a function of time in the streptozotocin induced diabetic mouse model in the same animals and treatment conditions shown in FIG. 4.

Percent Change in body weight data are presented in FIG. 5. No Significant differences were observed between the treatment groups and vehicle treated groups.

Subcutaneous administration of PanCyte and Linear-PanCyte at 50 µg/kg body weight for twenty eight days lowered blood glucose levels significantly as compared to vehicle in multiple low dose STZ induced diabetic mice. No significant differences were observed in percent body weight change.

This example shows that subcutaneous administration of 50 µg/kg body weight of either PanCyte or Linear-PanCyte for 28 days lowers blood glucose levels in an accepted model of diabetes. This example shows that both PanCyte and Linear-PanCyte are strong candidates for use in treating human diabetes as well.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

I claim:

1. A method of treating diabetes comprising administering to a subject who is suffering from or susceptible to diabetes an angiotensin (1-7) peptide selected from i) Asp$^1$-Arg$^2$-Val$^3$-Ser$^4$-Ile$^5$-His$^6$-Cys$^7$ (SEQ ID NO: 6); and ii) a cyclic peptide having the structure:

(SEQ ID NO: 22)

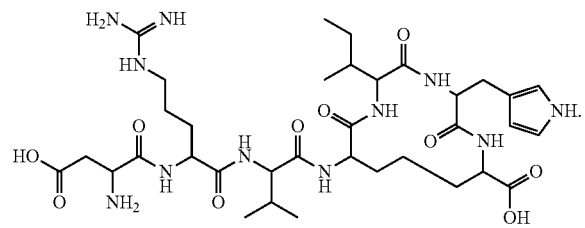

2. The method of claim 1, wherein the angiotensin (1-7) peptide is administered at an effective dose periodically at an administration interval such that at least one symptom or feature of diabetes is reduced in intensity, severity, duration, or frequency or has delayed in onset.

3. The method of claim 1, wherein the diabetes is selected from the group consisting of type 1 diabetes, type 2 diabetes, and gestational diabetes.

4. The method of claim 1, wherein the subject is suffering from pre-diabetes.

5. The method of claim 1, wherein the angiotensin (1-7) peptide is administered daily, twice a week, weekly, once every two weeks, once every three weeks, monthly, or at a variable interval.

6. The method of claim 1, wherein the angiotensin (1-7) peptide is administered intravenously, intradermally, orally, by inhalation, transdermally (topical), subcutaneously, and/or transmucosally.

7. The method of claim 1, wherein the angiotensin (1-7) peptide is administered at the effective dose ranging from about 1-1000 μg/kg/day.

8. The method of claim 1, wherein the administration of the angiotensin (1-7) peptide results in a 10%, 20%, 30%, 40%, or 50% reduction in fasting blood glucose levels in the subject as compared to a control.

9. The method of claim 1, wherein the administration of the angiotensin (1-7) peptide reduces the fasting glucose level in the subject to less than 130 mg/dL.

10. The method of claim 1, wherein the administration of the angiotensin (1-7) peptide results in a 20% decrease in blood glucose in the subject as compared to a control.

11. The method of claim 1, wherein the administration of the angiotensin (1-7) peptide reduces the blood glucose level in the subject to less than about 200 mg/dL.

12. The method of claim 1, wherein the administration of the angiotensin (1-7) peptide reduces the blood glucose level in the subject to within the normal range.

13. The method of claim 8, wherein the decrease or reduction of the glucose level is achieved within 1 month of treatment.

14. The method of claim 1, wherein the linear or cyclic angiotensin (1-7) peptide is administered in combination with an anti-diabetic medication.

15. The method claim 14, wherein anti-diabetic medication is selected from the group consisting of biguanides, thiazolidinediones, dual PPAR agonists, secretagogues including sulphonylureas, meglitinides/glinides (K+), incretin mimetics, DPP-4 inhibitors, insulin, insulin analogs or special formulations, alpha-glucosidase inhibitors, amylin or amylin analogues, SGLT2 inhibitors, Benfluorex, Tolrestat, or combinations thereof.

16. The method of claim 1, wherein the angiotensin (1-7) peptide is Asp$^1$-Arg$^2$-Val$^3$-Ser$^4$-Ile$^5$-His$^6$-Cys$^7$ (SEQ ID NO: 6).
17. The method of claim 1, wherein the angiotensin (1-7) peptide is
(SEQ ID NO: 22)
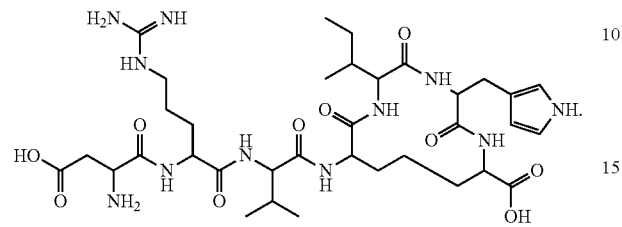
* * * * *

UNITED STATES PATENT AND TRADEMARK OFFICE
CERTIFICATE OF CORRECTION

PATENT NO.        : 8,557,958 B1                                Page 1 of 2
APPLICATION NO.   : 13/757475
DATED             : October 15, 2013
INVENTOR(S)       : Richard Franklin It is certified that error appears in the above-identified patent and that said Letters Patent is hereby corrected as shown below:

In the Claims

Please correct claims 1 and 17 as follows:

Col. 53, lines 40-50

In claim 1, please delete:

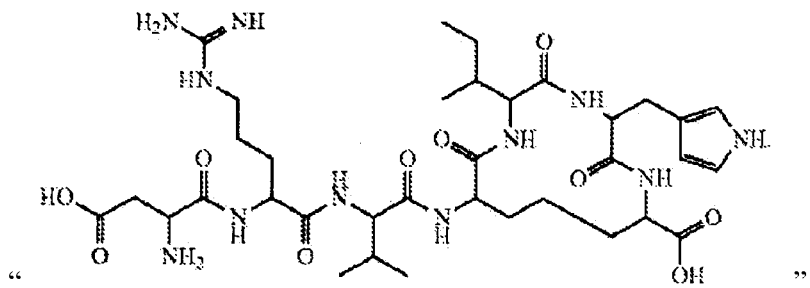

and replace it with:

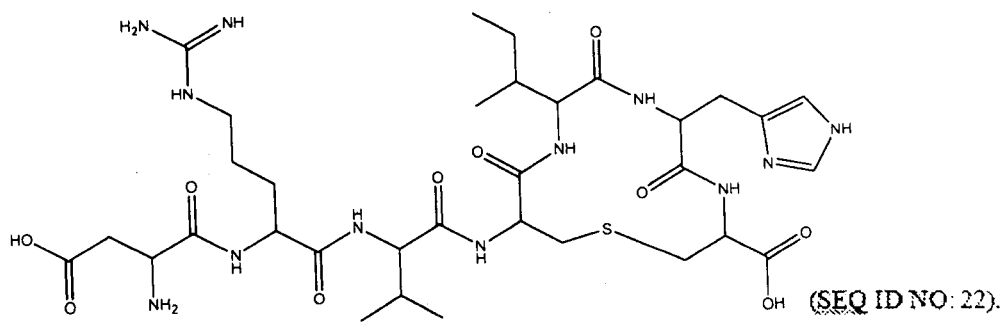

Signed and Sealed this
Twenty-sixth Day of November, 2013

Margaret A. Focarino
*Commissioner for Patents of the United States Patent and Trademark Office*

CERTIFICATE OF CORRECTION (continued)
U.S. Pat. No. 8,557,958 B1

Col. 55, lines 10-20

In claim 17, please delete:

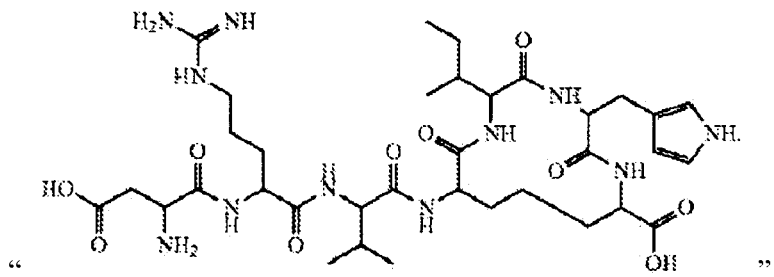

" "

and replace it with:

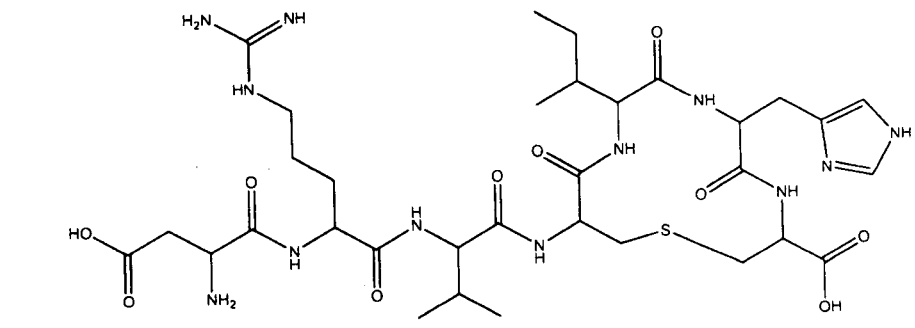

.